US012564331B2

(12) United States Patent
Park et al.

(10) Patent No.: US 12,564,331 B2
(45) Date of Patent: Mar. 3, 2026

(54) SENSOR LOCALIZATION IN A MAGNETOENCEPHALOGRAPHY (MEG) SYSTEM

(71) Applicant: FieldLine Inc., Boulder, CO (US)

(72) Inventors: Aaron Park, Boulder, CO (US); Orang Alem, Erie, CO (US); Svenja Knappe, Boulder, CO (US); Kendall D. Holloway, Denver, CO (US)

(73) Assignee: FieldLine Inc., Boulder, CO (US)

( * ) Notice: Subject to any disclaimer, the term of this patent is extended or adjusted under 35 U.S.C. 154(b) by 0 days.

(21) Appl. No.: 17/930,280

(22) Filed: Sep. 7, 2022

(65) Prior Publication Data

US 2023/0074561 A1    Mar. 9, 2023

Related U.S. Application Data

(60) Provisional application No. 63/241,341, filed on Sep. 7, 2021.

(51) Int. Cl.
| | |
|---|---|
| *A61B 5/06* | (2006.01) |
| *A61B 5/00* | (2006.01) |
| *A61B 5/245* | (2021.01) |
| *G01R 33/022* | (2006.01) |
| *G01R 33/032* | (2006.01) |

(52) U.S. Cl.
CPC .............. *A61B 5/065* (2013.01); *A61B 5/245* (2021.01); *A61B 5/6803* (2013.01); *G01R 33/022* (2013.01); *G01R 33/032* (2013.01); *A61B 2562/0223* (2013.01)

(58) Field of Classification Search
CPC . A61B 2562/0223; A61B 5/065; A61B 5/245; A61B 5/6803; G01R 33/022; G01R 33/032
See application file for complete search history.

(56) References Cited

U.S. PATENT DOCUMENTS

| | | | |
|---|---|---|---|
| 2018/0313908 A1 | 11/2018 | Knappe et al. | |
| 2019/0391213 A1 | 12/2019 | Alford | |
| 2021/0080519 A1 * | 3/2021 | Iwasaki | ................ G01R 33/098 |

OTHER PUBLICATIONS

International Search Report & Written Opinion for PCT Application PCTUS2022076034, mailed Feb. 14, 2023; 20 pages.
Pfeiffer Christoph et al: "On-scalp MEG sensor localization using magnetic dipole-like coils: A method for highly accurate co-registration", Neuroimage, Elsevier, Amsterdam, NL, vol. 212, Feb. 28, 2020.

* cited by examiner

*Primary Examiner* — Michael T Rozanski

(57) ABSTRACT

Various embodiments disclosed herein comprise systems and methods to locate magnetic field sensors. In some examples, a system comprises a controller, a sensor mount, a coil set comprising one or more coils, and a magnetic field sensor. The sensor mount mounts the magnetic field sensor and constrains at least one degree of freedom of the magnetic field sensor in position or orientation. The controller supplies electric current to the coil set. The coil set generates magnetic waves that form at least one coil magnetic field in response to receiving the current. The magnetic field sensor measures the strength of the coil magnetic field. The controller locates the magnetic field sensor based on the constraint and the measured strength of the coil magnetic field.

20 Claims, 11 Drawing Sheets

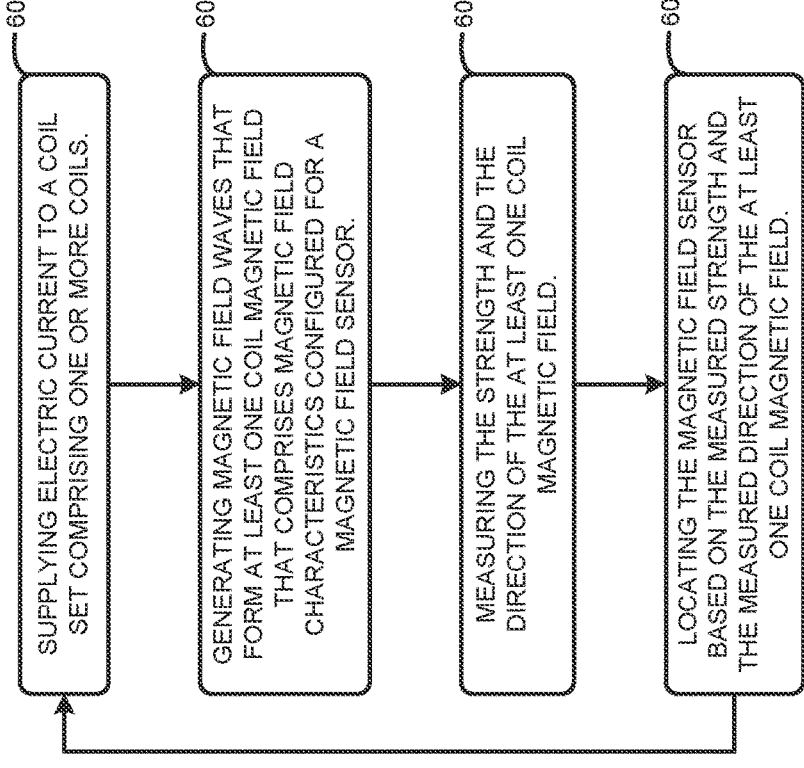

601

SUPPLYING ELECTRIC CURRENT TO A COIL SET COMPRISING ONE OR MORE COILS.

602

GENERATING MAGNETIC FIELD WAVES THAT FORM AT LEAST ONE COIL MAGNETIC FIELD THAT COMPRISES MAGNETIC FIELD CHARACTERISTICS CONFIGURED FOR A MAGNETIC FIELD SENSOR.

603

MEASURING THE STRENGTH AND THE DIRECTION OF THE AT LEAST ONE COIL MAGNETIC FIELD.

604

LOCATING THE MAGNETIC FIELD SENSOR BASED ON THE MEASURED STRENGTH AND THE MEASURED DIRECTION OF THE AT LEAST ONE COIL MAGNETIC FIELD.

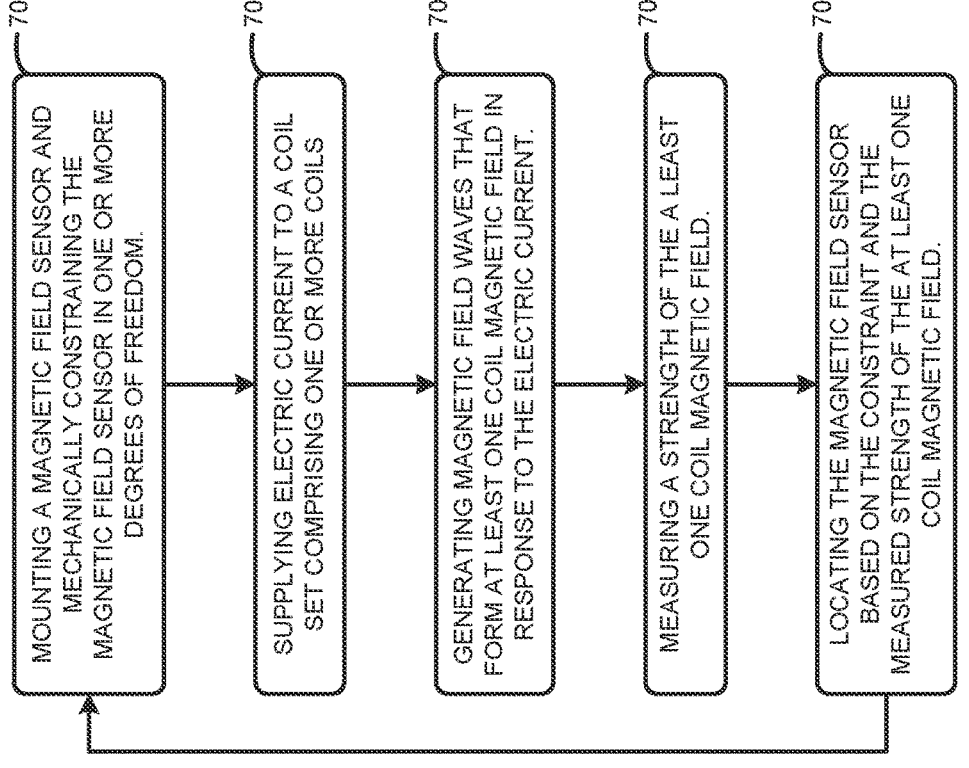

701 MOUNTING A MAGNETIC FIELD SENSOR AND MECHANICALLY CONSTRAINING THE MAGNETIC FIELD SENSOR IN ONE OR MORE DEGREES OF FREEDOM.

702 SUPPLYING ELECTRIC CURRENT TO A COIL SET COMPRISING ONE OR MORE COILS

703 GENERATING MAGNETIC FIELD WAVES THAT FORM AT LEAST ONE COIL MAGNETIC FIELD IN RESPONSE TO THE ELECTRIC CURRENT.

704 MEASURING A STRENGTH OF THE A LEAST ONE COIL MAGNETIC FIELD.

705 LOCATING THE MAGNETIC FIELD SENSOR BASED ON THE CONSTRAINT AND THE MEASURED STRENGTH OF THE AT LEAST ONE COIL MAGNETIC FIELD.

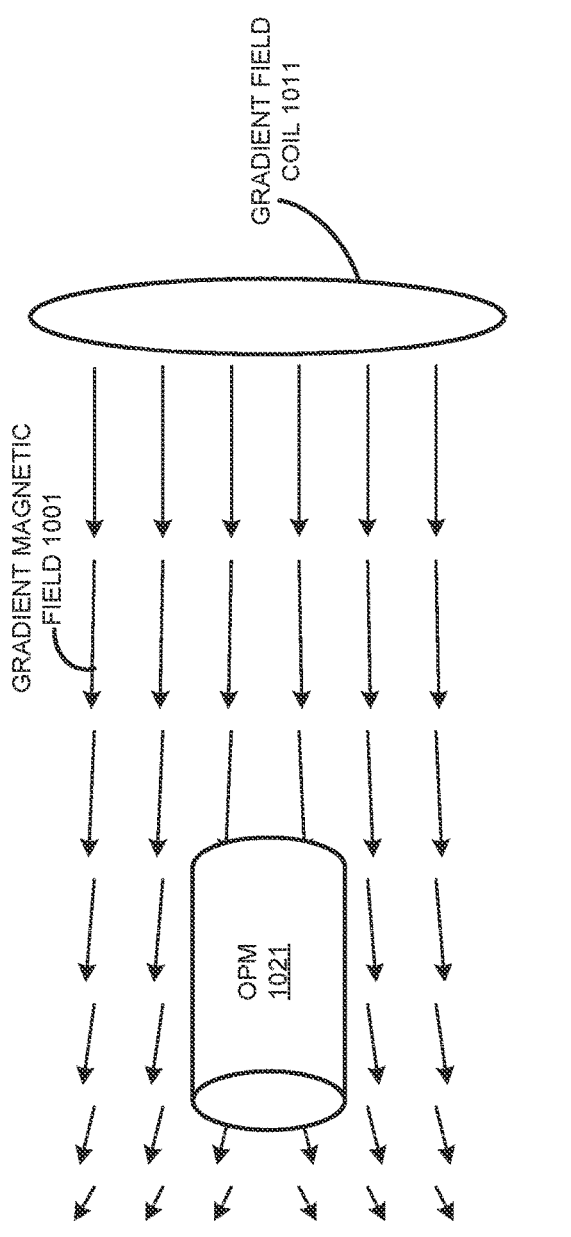
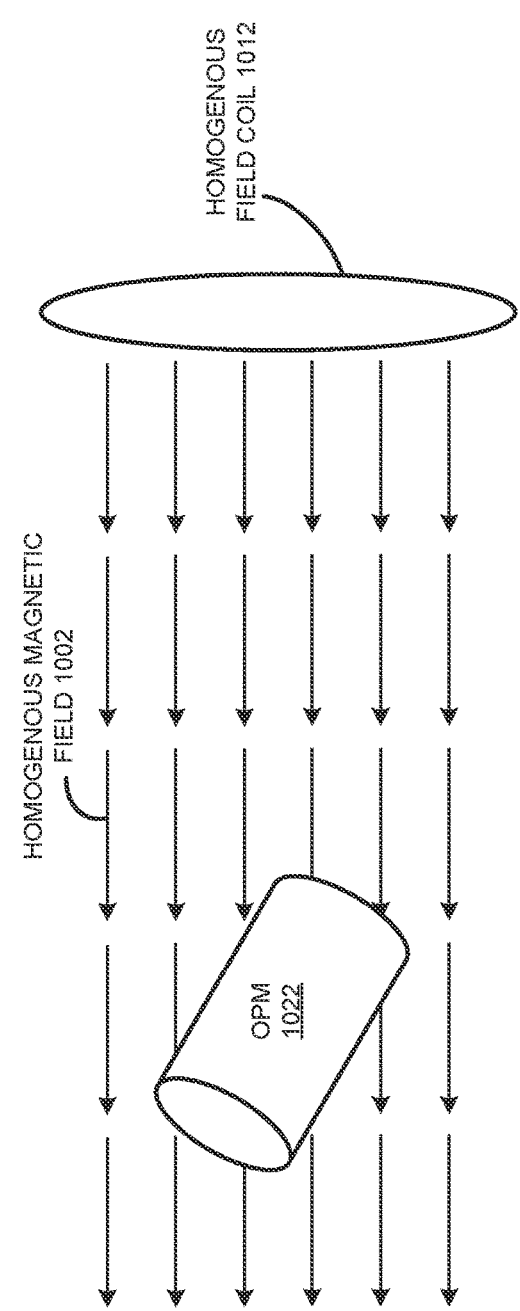
FIGURE 10

SENSOR LOCALIZATION IN A MAGNETOENCEPHALOGRAPHY (MEG) SYSTEM

RELATED APPLICATIONS

This U.S. patent application claims the benefit of and priority to U.S. Provisional Patent Application 63/241,341 entitled, "SENSOR LOCALIZATION IN AN OPTICALLY-PUMPED MAGNETOMETER (OPM) SYSTEM" which was filed on Sep. 7, 2021, and which is hereby incorporated by reference in its entirety into this U.S. patent application.

BACKGROUND

Magnetometer systems detect and characterize magnetic fields generated by a magnetic field source. The magnetometer systems measure the field strength and/or direction of the magnetic fields to characterize the sensed fields. Magnetoencephalography (MEG) systems are a type of magnetometer system that measures magnetic fields generated by neuronal activity within a subject's brain to map brain function. MEG systems image brain activity by detecting magnetic fields from neural currents using an array of magnetic sensors placed near the head of a subject and then computing the locations of the neural activity relative to the location of the sensor in a process referred to as source localization. Exemplary magnetic sensors used in the MEG systems include Optically Pumped Magnetometers (OPMs), however other magnetometer types like Superconducting Quantum Interference Devices (SQUIDs) may be used. The data from the sensors along with each sensor location is used to calculate the locations of neuronal signal sources to form MEG images of brain activity. For the source localization calculations, in addition to the data from the sensors, it is necessary to know the location and orientation of each sensor in a shared coordinate system.

Some MEG systems have sensors that can move independently and conform to the size and shape of the head. These MEG systems are referred to as on-scalp or conformal MEG. For conformal MEG systems, the location and orientation information for the sensor array is determined for every subject and every time the sensors are placed on the scalp to allow for accurate source localization of the neural activity in the brain. Since head shape and size varies from person to person, the locations and orientations of the sensors may change when performing conformal MEG on different subjects. Relocating the sensors and identifying their new locations and orientations is difficult and time-consuming process. Unfortunately, conformal MEG systems do not efficiently or effectively identify the spatial locations of the sensors.

Overview

This Overview is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Various embodiments of the present technology relate to solutions for localizing magnetic field sensors in Magnetoencephalography (MEG) systems. Some embodiments comprise a method to locate a magnetic field sensor. The method comprises supplying electric current to a coil set comprising one or more coils. The method further comprises generating magnetic waves that form at least one coil magnetic field that comprise magnetic field characteristics configured for a magnetic field sensor. The method further comprises measuring a strength and a direction of the at least one coil magnetic field. The method further comprises locating the magnetic field sensor based on the measured strength and the measured direction of the at least one coil magnetic field.

Some embodiments comprise a magnetic field detection system configured to localize magnetic field sensors. The system comprises a controller, a coil set comprising one or more coils, a sensor mount, and a magnetic field sensor. The sensor mount mounts the magnetic field sensor and mechanically constrains the magnetic field sensor in one or more degrees of freedom. The controller supplies electric current to the coil set comprising one or more coils. The coil set generates magnetic waves that form at least one coil magnetic field in response to receiving the electric current. The magnetic field sensor measures a strength of the coil magnetic field. The controller locates the magnetic field sensor based on the constraint and the measured strength of the coil magnetic field.

Some embodiments comprise a magnetic field detection system. The magnetic field detection system comprises one or more on-scalp magnetic field sensors, a sensor mount, and a hommock. The sensor mount positions the one or more magnetic field sensors with respect to a target magnetic field generated by a target. The hammock is operatively coupled to the sensor mount and holds the target. The target may comprise a human head and the sensor mount may be configured to surround the head. The hammock positions the target at a central location within the sensor mount and distributes the weight of the target.

DESCRIPTION OF THE DRAWINGS

Many aspects of the disclosure can be better understood with reference to the following drawings. The components in the drawings are not necessarily drawn to scale. Moreover, in the drawings, like reference numerals designate corresponding parts throughout the several views. While several embodiments are described in connection with these drawings, the disclosure is not limited to the embodiments disclosed herein. On the contrary, the intent is to cover all alternatives, modifications, and equivalents.

FIG. 6 illustrates an exemplary localization process.

FIG. 7 illustrates an exemplary localization process.

FIG. 10 illustrates exemplary magnetometers.

Figure 1:
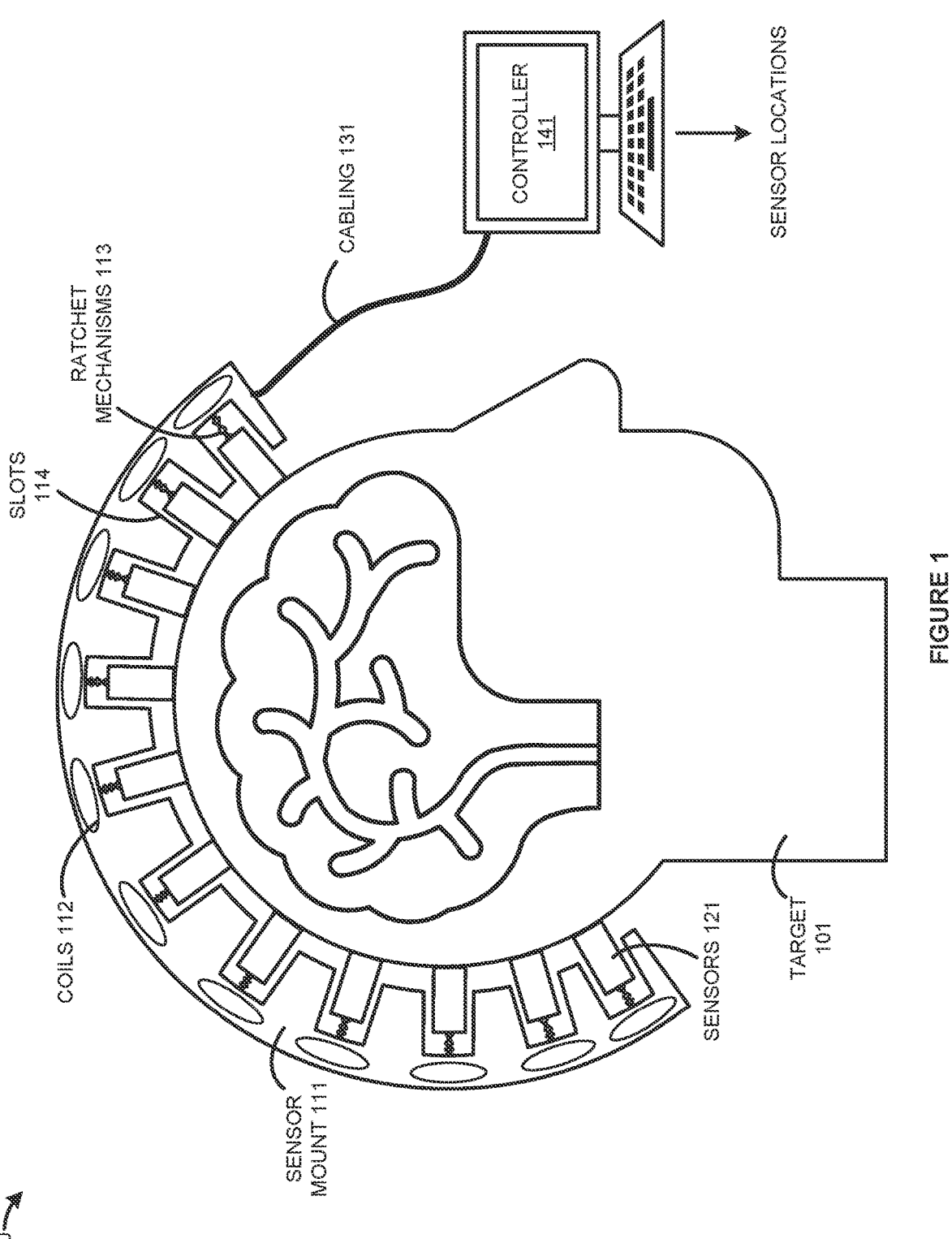
FIG. 1 illustrates an exemplary Magnetoencephalography (MEG) system.

The drawings have not necessarily been drawn to scale. Similarly, some components or operations may not be separated into different blocks or combined into a single block for the purposes of discussion of some of the embodiments of the present technology. Moreover, while the technology is amendable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

TECHNICAL DESCRIPTION

The following description and associated figures teach the best mode of the invention. For the purpose of teaching inventive principles, some conventional aspects of the best mode may be simplified or omitted. The following claims specify the scope of the invention. Note that some aspects of the best mode may not fall within the scope of the invention as specified by the claims. Thus, those skilled in the art will appreciate variations from the best mode that fall within the scope of the invention. Those skilled in the art will appreciate that the features described below can be combined in various ways to form multiple variations of the invention. As a result, the invention is not limited to the specific examples described below, but only by the claims and their equivalents.

The examples herein present systems and methods to localize magnetic field sensors in conformal Magnetoencephalography (MEG) systems. In the examples of conformal MEG systems provided herein, the sensors, like Optically Pumped Magnetometers (OPMs), conform to the shape a target subject (e.g., a human head). The sensors are mounted on headgear like a helmet or flexible cap that conforms the sensors to the scalp of the target subject. The headgear may constrain one or more positional or orientational degrees of freedom for each of the sensors. Sets of magnetic field sources are placed on or near the headgear. Each set of the magnetic field sources comprises one or more coils configured to generate a magnetic field with desired characteristics. The sets of magnetic field sources comprise known spatial locations that provide reference points for sensor localization. Moreover, each set of the magnetic field sources corresponds to one or more of the sensors mounted on the headgear. The magnetic field sources generate magnetic fields, and their corresponding sensor(s) measures the strength and/or direction of the generated fields. The measured magnetic field strength is correlated to a distance between the magnetic field source and the magnetic field sensor. The measured magnetic field direction may be correlated to a sensor orientation. The spatial location and orientation of the sensor is then determined based on the distance between the sensor and the magnetic field source, the known spatial location of the magnetic field source, and the orientation of the sensor. The orientation of the sensor may be determined based on the measured field direction. However, the orientation of the sensor may also be determined based on the positional and orientation constrains imposed on the sensors by the headgear. Correlating each set of magnetic field sources to one or more sensors allows for quick and efficient sensor localization. The increased efficiency reduces the time needed to localize the sensors and in turn, reduces the total amount of time needed to generate MEG images. The increased efficiency additionally reduces the amount of time a patient needs to wear the MEG headgear. Moreover, the correlation between each set of magnetic field sources and the one or more sensors improves the precision of the sensor localizations. The increased precision in the sensor localizations increases the accuracy and quality of MEG images generated from the sensor measurements. Now turning to the Figures.

FIG. 1 illustrates Magnetoencephalography (MEG) system 100 in a cross-sectional view. MEG system 100 performs operations like detecting magnetic fields and relating the detecting magnetic fields to neuronal activity for use in medical applications. Exemplary medical applications include identifying brain activity and diagnosing medical conditions like stroke, epilepsy, neuronal injuries, neuronal disorders, and/or other types of medical conditions relating to brain/neuron activity. MEG system 100 comprises target 101, sensor mount 111, coils 112, ratchet mechanisms 113, slots 114, sensors 121, cabling 131, and controller 141. In other examples, MEG system 100 may differ. In this example, target 101 comprises a human head however target 101 may comprise any magnetic field source including non-biological magnetic field sources.

Sensor mount 111 is representative of a conformal MEG apparatus. Sensor mount 111 comprises a wearable headgear configured to position sensors 121 in locations proximate to target 101. For example, sensor mount 111 may securely adhere sensors 121 to the scalp of target 101 using mechanical constraints. Sensor mount 111 may comprise a rigid helmet or a flexible cap. In this example, sensor mount 111 comprises a rigid helmet. Sensor mount 111 may be contrasted from rigid plastic, carbon fiber, polymer, or other types of materials that provide structural support to sensor mount 111 and that do not interfere in the magnetic sensing operations of sensors 121. Slots 114 form channels that control one or more degrees of freedom in the position and orientation of sensors 121. For example, slots 114 may be shaped to constrain the three orientational degrees of freedom for each of sensors 121 and two of the three locational degrees of freedom for each of sensors 121 allowing for each of sensors 121 to move along a single axis of motion. Sensor mount 111 conforms to the shape the target 101. For example, when target 101 comprises a human head, sensor mount 111 is shaped to conform to the geometry of a human head, however the shape of sensor mount 111 nor the type of target are limited.

Ratchet mechanisms 113 couple sensors 121 to sensor mount 111 in slots 114 and are configured to control one or more degrees of freedom in the position and orientation of sensors 121. Ratchet mechanisms may comprise set screws, springs, pistons, pneumatics, and the like. As stated above, slots 114 may be shaped to constrain the three orientational degrees of freedom and two of the three locational degrees of freedom for each of sensors 121. In this example, ratchet mechanisms 113 may control the last locational degree of freedom for each of sensors 121 to move each of sensors 121 through slots 114 along their respective axes of motion to desired locations. Senor mount 121 is placed on the head of target 101. Ratchet mechanisms 113 propel sensors 121 through their respective ones of slots 114 to their desired locations. For example, set screws in ratchet mechanisms 113 may be tightened to move sensors 121. Once at the desired location (e.g., sensor contact with target 101), ratchet mechanisms 113 may lock to secure sensors 121 at their desired locations. Once locked, all six of the orientational and locational degrees of freedom for sensors 121 are fixed. In alternate examples, sensors 121 instead protrude from sensor mount 111 and retract into slots 114 along their axes of motion when sensor mount 111 is worn by target 101. For example, sensor mount 111 may be placed onto the head of a target 101 and the head may force sensors 121 into slots 114. In this case, ratchet mechanism 113 may comprise springs that allow sensors 121 to compress into slots 114 in response to sensor mount 111 being worn by target 101.

In some examples, sensor mount 111 may instead comprise a flexible cap. In this case, the flexible cap may comprise an elastic material like rubber, elastic fabric, and the like. The flexible cap may be placed on the head of target

101. The flexible cap forms naturally to the shape of target 101 and compresses sensors 121 onto the scalp of target 101 to fix in place both the position and orientation of sensors 121. In the case where sensor mount 111 comprises a flexible cap, slots 114 and ratchet mechanisms 113 may be replaced with different slots that hold sensors 121 and restrict their movement. In either example, sensor mount 111 conforms sensors 121 to the surface of target 101. Although sensor mount 111 is illustrated conforming sensors 121 to the head of target subject 101, in other examples, sensor mount 111 may be shaped differently and conform sensors 121 another body part of interest like the abdomen. In some examples, sensor mount 111 may comprise support elements like padding, straps, cushions, and/or some other type of the support system to support and position the head of target 101 within sensor mount 111. In some examples, sensor mount 111 is worn by target 101. In alternate examples, sensor mount 111 is stationary, and target 101 is instead positioned within a magnetic field detection zone of sensors 121.

Sensor mount 111 further comprises coils 112. Coils 112 comprise loops of metallic wiring that generate an electromagnetic field in response to receiving electric current. Coils 112 may comprise single or multiple loops of any shape and size. Coils 112 may comprise sets of separated coils with differing loops of varying shapes, sizes, and orientations. The orientations and spatial configuration of the sets of separated coils may vary from set to set. In this example, coils 112 are embedded into the surface of the sensor apparatus. Coils 112 are stationary with respect to each other. Individual ones of coils 112 correspond to individual ones of sensors 121 on a one-to-one basis. In other examples, multiple ones of coils 112 may correspond to a single one of sensors 121 on a many-to-one basis. In other examples, individual ones of coils 112 may correspond to multiple ones of sensors 121 on a one-to-many basis. When exposed to an electric potential, coils 112 generate magnetic waves that form coil magnetic fields. Sensors 121 may measure the coil magnetic fields and report the field strength to controller 141. Controller 141 may determine the location of sensors 121 based on the reported field strengths, the orientational and locational constraints, and the locations of coils 112. Although coils 112 are illustrated embedded in sensor mount 111, in other examples some or all of coils 112 may reside at fixed locations external to sensor mount 111. For example, in the case where sensor mount 111 comprises a flexible cap, coils 112 may be positioned external to sensor mount 111 at locations proximate to sensors mount 111.

In some examples, MEG system 100 does not include sensor mount 111 and sensors 121 may be conformed to the head of target in another way. For example, sensors 121 may be directly adhered to the scalp of target 101 using tape, glue, or another type of temporary adhesive to form an on-scalp sensor array. In these examples, coils 112 reside at known spatial locations and orientations external to target 101 where sensors 121 correspond to coils 112 on a one-to-one, many-to-one, or one-to-many basis.

Sensors 121 comprise magnetometers that sense magnetic fields generated by a magnetic field source in target 101 and coil magnetic fields generated by coils 112. Sensors 121 generate signals that characterize the strength of the detected magnetic fields. In this example, the magnetic field source comprises the brain of target 101. The neuronal activity in the brain of target 101 comprises intercellular electromagnetic signals. Sensors 121 sense the magnetic component of the electromagnetic signals to detect the neuronal activity. Sensors 121 form a sensor array that is contoured to the head of target 101 by sensor mount 111. Exemplary magnetometers that may comprise sensors 121 include Optically Pumped Magnetometers (OPMs), atomic magnetometers, gradiometers, nitrogen vacancy centers, high-temperature Superconducting Quantum Interference Devices (SQUIDs), and the like.

Sensors 121 are coupled to controller 141 over cabling 131. Cabling 131 comprises sheathed metallic wires. For example, sensors 121 may transfer signaling that characterizes the sensed magnetic field to controller 141 over cabling 131. In some examples, cabling 131 may be replaced with, or used in addition with, a wireless transceiver system (e.g., antennas) to transfer communications between controller 141 and sensors 121 over a wireless networking protocol like bluetooth.

Controller 141 is representative of one or more computing devices configured to drive the operation of sensors 121 and coils 112 and to localize sensors 121 and to generate MEG images depicted the measured neuronal activity in target 101. The one or more computing devices comprise processors, memories, and transceivers that are connected over bus circuitry. The processors may comprise Central Processing Units (CPUs), Graphical Processing Units (GPUs), Digital Signal Processors (DSPs), Application Specific Integrated Circuits (ASICs), Field Programmable Gate Arrays (FPGAs), and the like. The memories may comprise Random Access Memory (RAM), flash circuitry, Solid States Drives (SSDs), Hard Disk Drives (HDDs), and the like. The memory stores software like operating systems, MEG applications, localization applications, sensor data, and the like. The processors retrieve and execute the software from the memory to drive the operation of controller 141.

When sensors 121 are conformed to the shape of target 101, controller 141 supplies electric current to a set of coils 112. The set comprises one or more coils that correspond to one of sensors 121. The set of coils 112 responsively generates magnetic waves that form one or more coil magnetic fields. The one or more magnetic fields may comprise different frequencies, different phases, or the same frequencies and the same phases. The one or more magnetic fields may comprise homogenous magnetic fields and gradient magnetic fields. A homogenous magnetic field is constant in both field magnitude and direction over a region of interest while a gradient magnetic field varies in either or both magnitude and direction over a region of interest. The one or more magnetic fields may be combined into a single magnetic field that comprises field characteristics configured for a particular one of sensors 121. Controller 141 transfers instructions to the one of sensors 121 that corresponds to the set of coils 112. The one of sensors 121 receives the instructions and responsively measures the one or more coil magnetic fields and reports sensor data characterizing the one or more coil magnetic fields strength to controller 141. The sensor data may comprise field strengths, measured field gradients, field orientation and direction, and/or other attributes of the one or more coil magnetic fields. Controller 141 correlates the reported magnetic field characteristics to a location and/or orientation of the one of sensors 121. Controller 141 may repeat this process to determine the location and/or orientation of all of sensors 121.

Once sensors 121 are located, controller 141 stops sending power to coils 112. Controller 141 transfers instructions to sensors 121 that direct sensors 121 to measure a magnetic field generated by neuronal activity in target 101 over cabling 131. Controller 141 receives sensor data from sensors 121 that characterizes the strength and/or other field attributes of the sensed magnetic field. The sensor data may be addressed (e.g., sensor ID) to correlate the measured magnetic field strengths with individual ones of sensors 121. Controller 141 executes a MEG application that performs source localization to generate a MEG image based on the target magnetic field strengths measured by sensors 121 and the spatial locations for each of sensors 121. The MEG image depicts the magnetic field detected by sensors 121 in three dimensions to illustrate the neuronal activity in the brain of target 101.

Advantageously, MEG system 100 efficiently locates sensors 121. Moreover, MEG system 100 effectively controls the operation of coils 112 and sensors 121 to correlate measured magnetic field characteristics and mechanical constrains of sensors 121 to spatial locations of sensors 121. The coil-to-sensor functional relationships between ones of sensors 121 and coil sets of coils 112 creates reference points that controller 141 uses to identify the locations of sensors 121.

Although the above examples are discussed with relation to Magnetoencephalography (MEG), other magnetic imaging modalities are contemplated herein. For example, MEG system 100 may instead comprise a Magnetocardiography (MCG) system, a Magnetogastrography (MGG) system, a Magnetomyography (MMG) system, or another type of anatomical magnetic sensing technology.

In some examples, MEG system 100 implements process 600 illustrated in FIG. 6. In some examples, MEG system 100 implements process 700 illustrated in FIG. 7. It should be appreciated that the structure and operation of MEG system 100 may differ in other examples.

Figure 2:
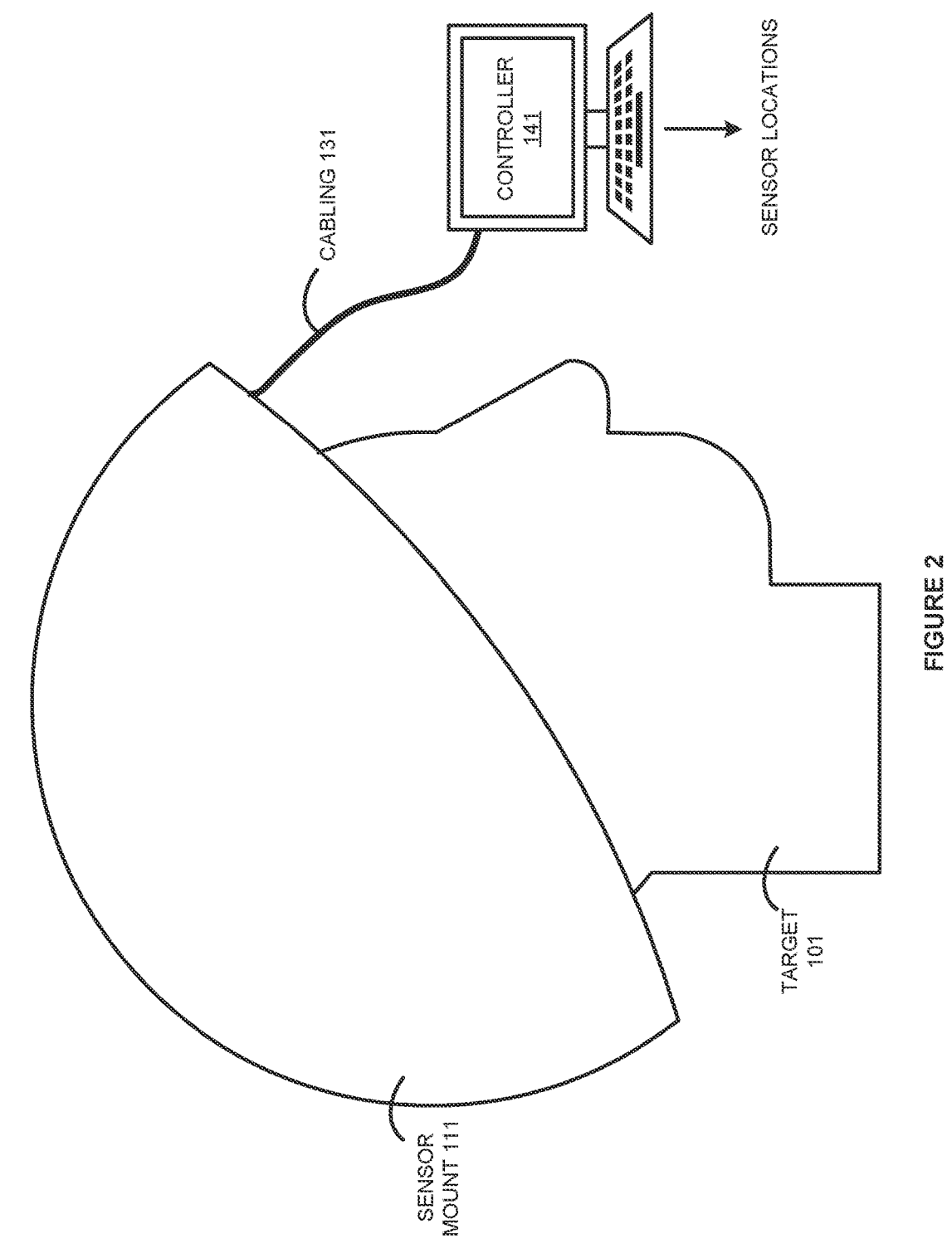
FIG. 2 illustrates an exemplary MEG system.

FIG. 2 illustrates view 200. View 200 comprises an external perspective of MEG system 100. View 200 comprises target 101, sensor mount 111, cabling 131, and controller 141. While present, the view of coils 112, ratchet mechanisms 113, slots 114, and sensors 121 is obstructed by the outer surface of sensor mount 111. As illustrated in FIG. 2, sensor mount 111 is worn by target 101 and surrounds or otherwise encloses the region of interest in target 101. In this case, the region of interest comprises neuronal activity in the brain of target 101. In some examples, portions of coils 112, ratchet mechanisms 113, slots 114, and/or sensors 121 may be visible on the outer surface of sensor mount 111. For example, an upper section of ratchet mechanisms 113 may protrude from the outer surface of sensor mount 111 to allow for an operator to interact with (e.g., tighten set screws) ratchet mechanisms 113.

Figure 3:
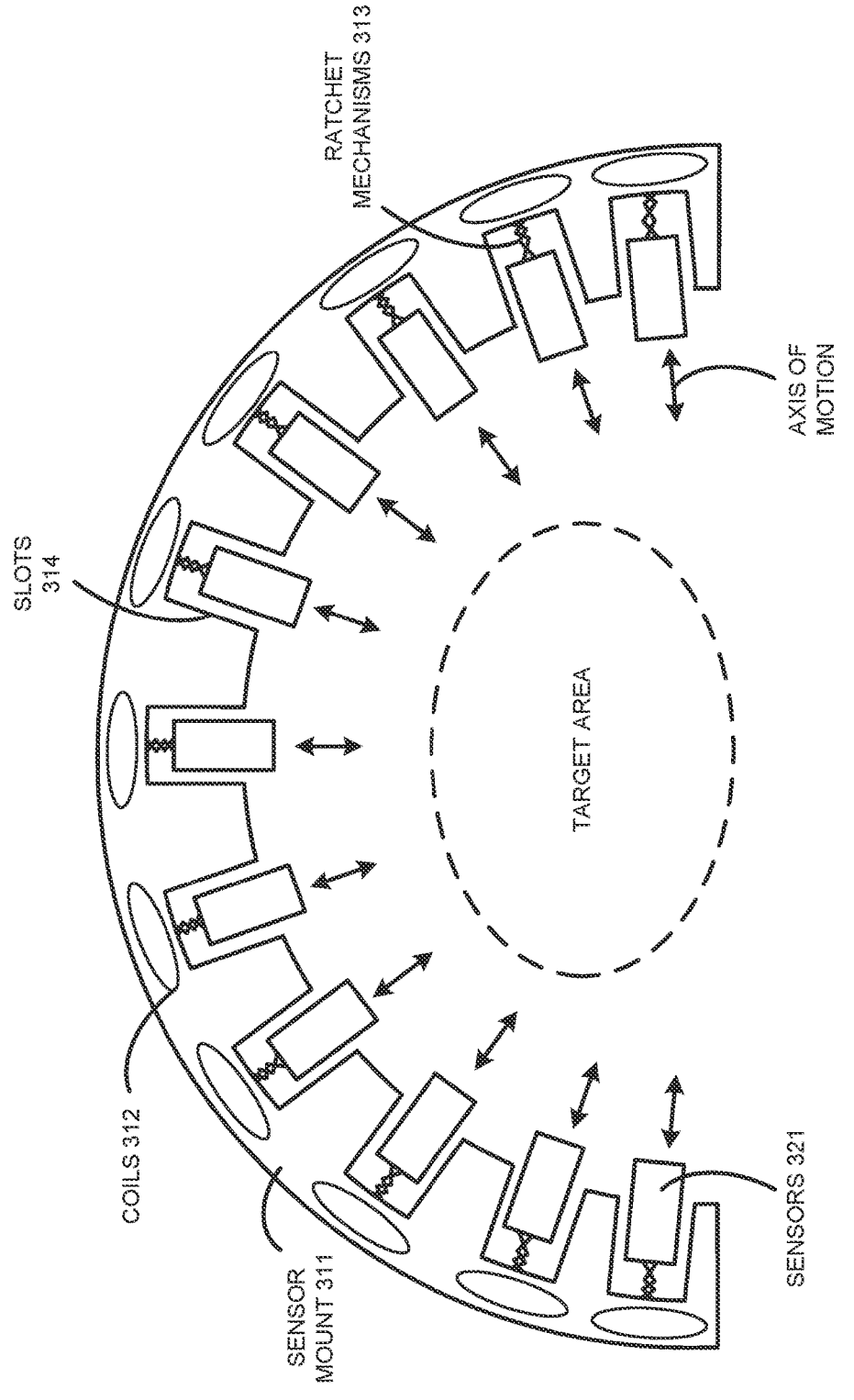
FIG. 3 illustrates an exemplary sensor mount.

FIG. 3 illustrates environment 300. Environment 300 comprises a cross-sectional view of sensor mount 311. Sensor mount 311 is representative of a conformal MEG helmet. Sensor mount 311 comprises coils 312, ratchet mechanisms 313, slots 314, and sensors 321. Sensor mount 311 is an example of sensor mount 111 illustrated in FIG. 1, however sensor mount 111 may differ. Sensor mount 311 is an example of a wearable conformal MEG apparatus where a subject wears the apparatus on their head.

Sensor mount 311 comprises a conformal MEG helmet constructed from rigid plastic, carbon fiber, rigid polymer, or other materials that do not inhibit magnetic sensing of a magnetic field generated by neuronal activity in a target subject and magnetic fields generated by coils 312. For example, sensor mount 311 may comprise a 3D printed construction. Sensors 321 comprise magnetometers like OPMs, gradiometers, nitrogen vacancy centers, SQUIDs, and/or other types of magnetic sensing devices. For example, sensors 321 detect and measure magnetic fields generated by neuronal activity of the human brain when sensor mount 311 is worn by a patient. Sensors 321 reside in slots 314. Slots 314 comprises indented regions in sensor mount 311 shaped to house sensors 321. For example, if sensors 321 are cylindrically shaped, slots 314 may comprise cylindrically shaped indentations that correspond to the shape and size of sensors 321. The shape of slots 314 constrains the three orientational degrees of freedom for sensors 321 and constrains two of the three positional degrees of freedom for sensors 321. Sensors 321 may move in the unconstrained positional degree of freedom along their respective axes of motion as illustrated in FIG. 3. The unconstrained positional degree of freedom of sensors 321 aligns with the longitudinal direction of slots 314.

Sensors 321 are coupled to sensor mount 311 via ratchet mechanisms 313. Ratchet mechanisms 313 are housed in slots 314. Ratchet mechanisms 313 may comprise set screws, springs, pistons, pneumatics, and/or other mechanical systems configured to move sensors 321 along their respective axes of motion. Ratchet mechanisms 313 are adjusted to move sensors 321 through slots 314 along their respective axes of motion until in contact with, or proximate to, a target subject. For example, ratchet mechanisms 313 may comprise actuators and electronic pistons. An actuator may receive control signaling and in response, drive an electronic piston to move one of sensors 321 through a corresponding one of slots 314 until in contact with the scalp of a target subject. For example, ratchet mechanisms 313 may comprise set screws. A set screws may be rotated to drive one of sensors 321 through a corresponding one of slots 314 until in contact with the scalp of a target subject. Once at their desired locations, ratchet mechanisms 313 are locked. When locked, ratchet mechanisms 313 and slots 314 constrain the position and orientation of sensors 321 to conform to the target subject.

Coils 312 are embedded into sensor mount 311 at known locations. Coils 312 comprise metallic loops (e.g., copper wiring) that generate magnetic fields with desired characteristics when connected to an electric potential. Individual ones of coils 312 correspond to individual ones of sensors 321 and slots 314 on a one-to-one basis. The position and orientation of coils 312 is aligned with their corresponding ones of sensors 321. Coils 312 generate gradient magnetic fields for corresponding ones of sensors 321. The gradient magnetic fields are directionally aligned with the axis of motion of their respective ones of sensors 321 while the magnitude of the gradient magnetic fields varies along the axis of motion of their respective ones of sensors 321. As such, the field strength measured by sensors 321 changes as sensors move along their axes of motion. The measured field strength may be correlated to a distance between coils 312 and sensors 321. Since the location and orientation of coils 312 and slots 314 are known and each of coils 312 and slots 314 correspond to sensors 121 on a one-to-one basis, the spatial locations of sensors 321 may be determined based on correlated distance and the constrained orientational and locational degrees of freedom of sensors 321.

Figure 4:
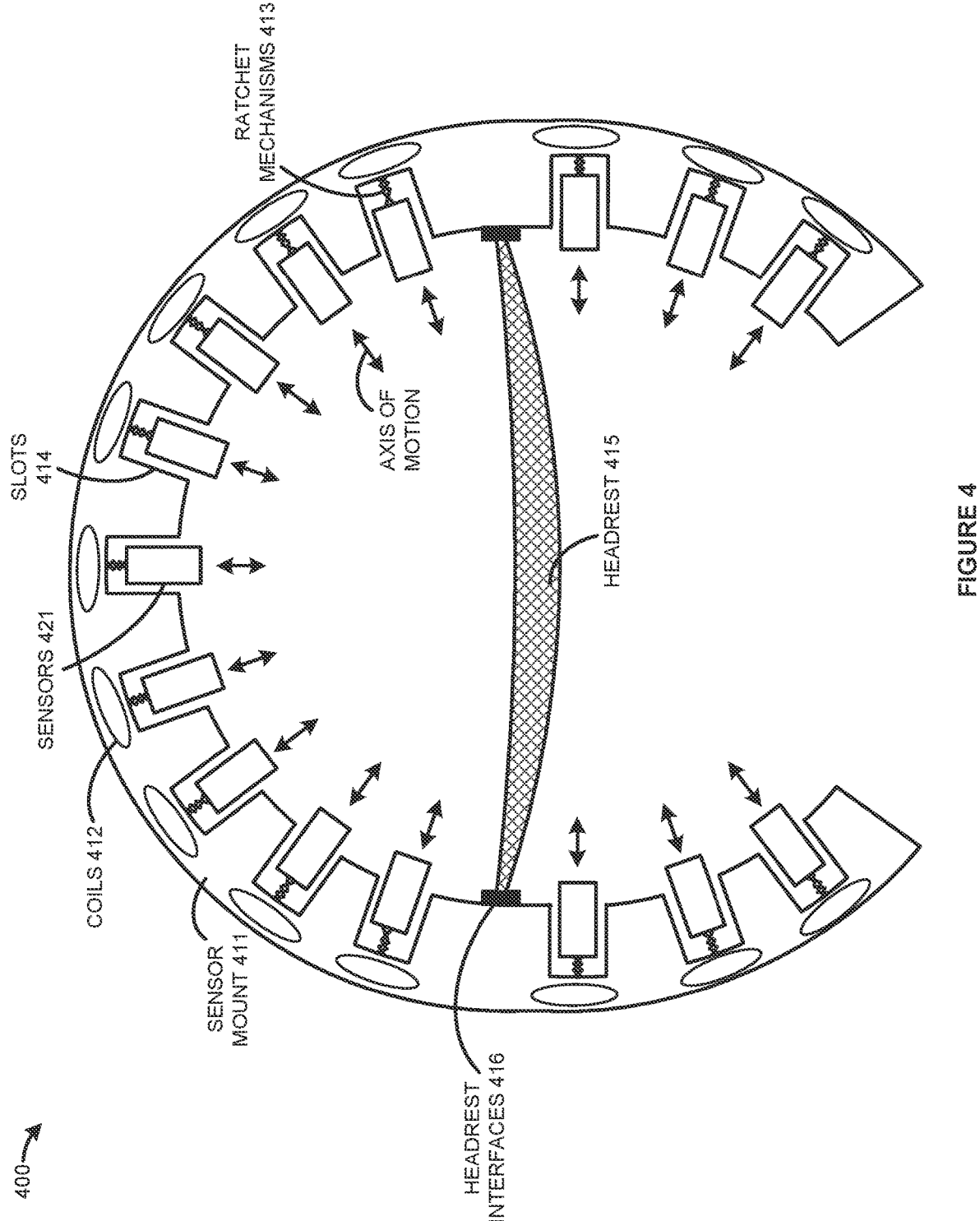
FIG. 4 illustrates an exemplary sensor mount.

FIG. 4 illustrates environment 400. Environment 400 comprises a cross-sectional view of sensor mount 411. Sensor mount 411 is representative of a conformal MEG helmet. Sensor mount 411 comprises sensor coils 412, ratchet mechanisms 413, slots 414, headrest 415, headrest interfaces 416, and sensors 421. Sensor mount 411 is an example of sensor mount 111 illustrated in FIG. 1, however sensor mount 111 may differ. Sensor mount 411 is an example of a stationary conformal MEG apparatus where a target is placed within the apparatus as opposed to a wearable MEG helmet like sensor mount 311 illustrated in FIG. 3.

Sensor mount 411 comprises a stationary conformal MEG helmet constructed from rigid materials that do not inhibit magnetic sensing operations of sensors 421. Sensors 421 comprise magnetometers like OPMs that reside in slots 414. Slots 414 comprise shaped indentations that correspond to the shape and size of sensors 421. The shape of slots 414 constrains the orientation and position of sensors 421. Sensors 421 are coupled to sensor mount 411 via ratchet mechanisms 413 that are housed in slots 414. Sensors 421 may move through slots 414 in response to action by ratchet mechanisms 413 along their respective axes of motion as illustrated in FIG. 4. Ratchet mechanisms 413 may comprise set screws, springs, pistons, pneumatics, and the like. Once sensors 421 are at their desired locations (e.g., proximate to a target subject), ratchet mechanisms 413 are locked. When locked, ratchet mechanisms 413 and slots 414 constrain the position and orientation of sensors 421 to conform to the shape of the target subject. Coils 412 are embedded into sensor mount 411 at known locations. Coils 412 comprise metallic loops that generate magnetic fields with desired characteristics when connected to an electric potential. Individual ones of coils 412 correspond to individual ones of sensors 421 on a one-to-one basis. The coil magnetic field strength measured by sensors 421 changes as sensors move along their axes of motion. The measured field strength may be correlated to a distance between coils 412 and sensors 421 to determine the spatial locations of sensors 421.

As stated above, sensor mount 411 comprises a stationary MEG apparatus. Headrest 415 comprises a support element configured to hold the head of a target within sensor mount 411 when a target in positioned within sensor mount 411. For example, a human may lay in a prone position with their head inside of sensor mount 411, and headrest 415 may cradle the human's neck to support the weight of the head. Headrest 415 is representative of a hammock or sling and may comprise fabrics, a meshes, straps, ropes, netting, flexible plastics, and/or another type of support structures configured to support a human head, neck, or other body part of interest. Headrest 415 may comprise compressible elements like padding or cushions to provide additional support and comfort to the target. Headrest 415 positions target at a central position within sensor mount 411. The central position allows sensors 421 to contact the head of the target. Headrest 415 distributes the weight of the target to provide support and increase the comfort of the target. For example, a human may place their head within sensor mount 411. The human may rest their head on headrest 415. Headrest 415 supports the head of the human and positions the head in a central location within sensor mount 411. Headrest interfaces 416 attach headrest 415 to sensor mount 411. Headrest interfaces 416 may comprise hook and loop fasteners, stiches, screws, and the like.

In examples where sensor mount 411 is configured to perform another magnetic imaging technique for of other body parts like the chest (e.g., magnetocardiography) or abdomen (e.g., magnetogastrography), sensor mount 411 may be shaped to conform to the body part of interest. Likewise, headrest 415 may be shaped to conform and provide structural support to the body part of interest. For example, in MCG applications, headrest 415 may take the form of a chest rest to cradle the patient's chest and position the patient's chest within a central location of sensor mount 411.

Figure 5:
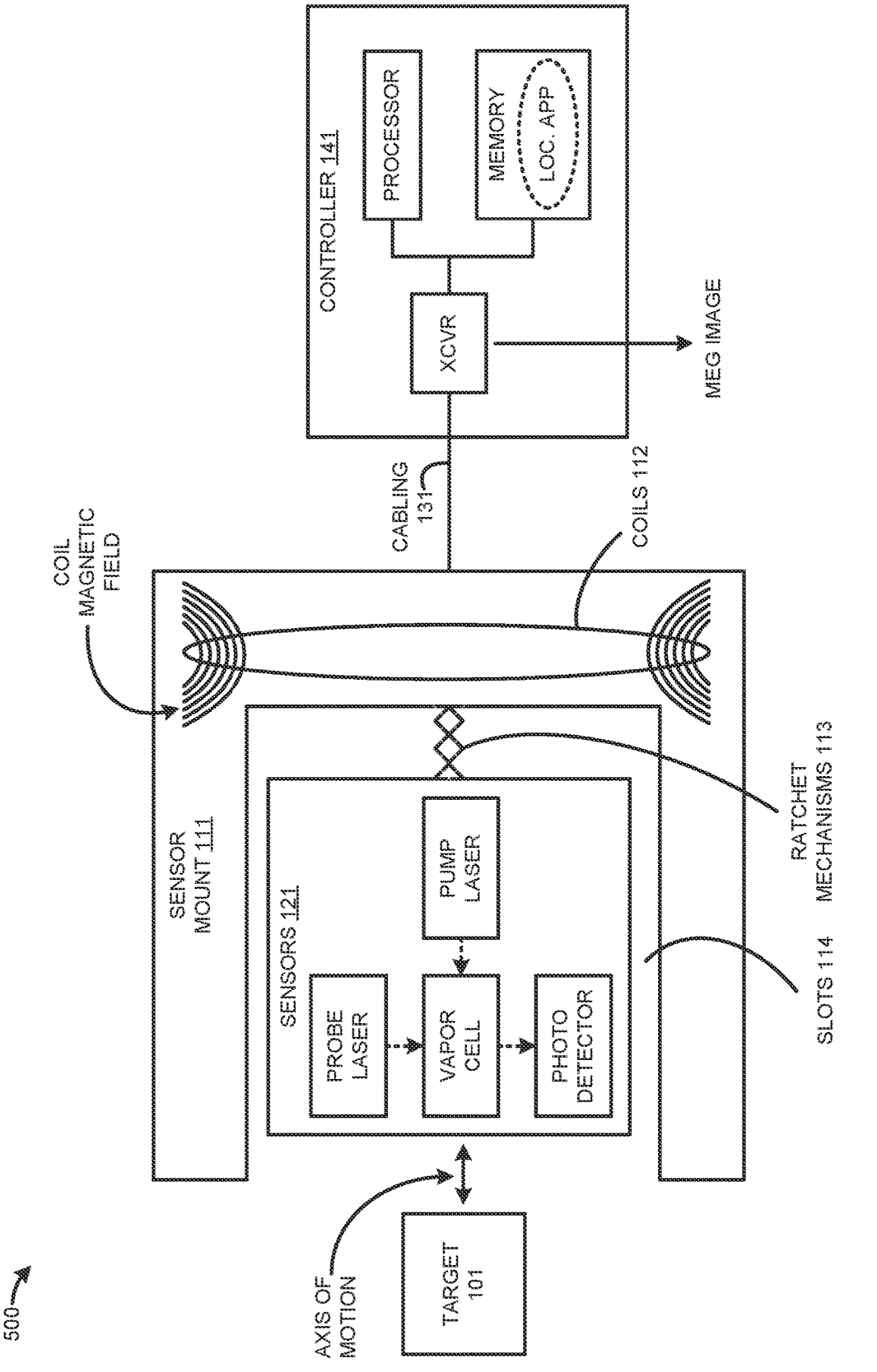
FIG. 5 illustrates an exemplary MEG system.

FIG. 5 illustrates environment 500. Environment 500 comprises a schematic view of MEG system 100 illustrated in FIG. 1. Environment 500 comprises target 101, sensor mount 111, coils 112, ratchet mechanisms 113, slots 114, sensors 121, cabling 131, and controller 141. Sensors 121 comprise a probe laser(s), a pump laser(s), a vapor cell(s), and a photo detector(s). Sensors 121 may optionally comprise bias coils and heaters. Controller 141 comprises transceiver (XCVR) circuitry, a processor, and a memory connected over bus circuitry. The memory stores a localization application (LOC. APP). Controller 141 typically comprises additional components like user interface systems and a power supply, however the additional components are omitted for the sake of clarity. In the following example, some of the elements that comprise MEG system 100 are referred to in the singular for the sake of clarity.

Sensor mount 111 may comprise a helmet, flexible cap, or another type of device that holds sensor 121, coil 112, and ratchet mechanism 113. Target 101 is magnetically linked to sensor 121. Coil 112 is magnetically linked to sensor 121. Sensor 121 and coil 112 are metallically linked to cabling 131 which is metallically linked to transceiver circuitry in controller 141. Cabling 131 may be detachably coupled to controller 141. Cabling 131 has a ground shield that is coupled to the ground in sensor 121 and to the ground in controller 141. Typically, additional sensors, cables, and coils are coupled to the controller 141, however they are omitted for clarity. Coil 112 is embedded into sensor mount 111. Coil 112 comprises a metal, metalloid, and/or some other type of material that generates a magnetic field in response to an electric current. Coil 112 surrounds and is perpendicular to the axis of motion of sensor 121. Coil 112 may comprise additional electronics like resistors, transistors, and the like. Coil 112 receives electric current from controller 141 over cabling and responsively generates the coil magnetic field.

Sensor 121 is representative of a magnetometer and comprises a pump laser and a probe laser. In some examples, the two lasers may be combined and/or additional lasers may be used. Sensor 121 also includes one or more vapor cells, and photodetectors. Sensor 121 may include signal processors and other electronics, but they are omitted in this example. Sensor 121 moves in response to action by ratchet mechanism 113 along its axis of motion through slot 114 to contact target 101. The axis of motion of sensor 121 algins with the axial direction of coil 112. Ratchet mechanism 113 may comprise a spring, pneumatic, electronic piston, set screw, and the like.

Controller 141 comprises a transceiver (XCVR) circuitry, memory, and a processor. The processor comprises an CPU, GPU, DSP, FPGA, ASIC, and/or some other type of processing circuitry. The memory comprises RAM, HDD, SSD, and the like. The memories store software like operating systems, localization application, coil location data, coil/sensor relationships, coil/slot relationships, and the like. The processors retrieve the software from the memory and execute the software to drive the operation of the MEG system 100 as described herein. The processor may write and read operational data to and from the memory. The operational data includes sensor IDs, coil loop locations, magnetic field strength, configuration parameters, and sensor performance characteristics.

In operation, sensor mount 111 is positioned near the magnetic field source of target 101. Controller 141 supplies electrical current to coil 112 and sensor 121 over cabling 131. Coil 112 generates magnetic waves that form the coil magnetic field. The magnitude of the magnetic field changes along the axis of motion of sensor 121. Typically, the measured strength of the coil magnetic field decreases as the distance between sensor 121 and coil 112 increases. Likewise, the measured strength of the coil magnetic field increases as the distance between sensor 121 and coil 112 decreases. Ratchet mechanism 113 moves sensor 121 through slot 114 along its axis of motion until sensor 121 contacts target 101. Once in contact with target 101, controller 141 transfers control signaling to sensor 121 to measure the coil magnetic field strength. For example, the processor of controller 141 may retrieve sensor/coil relationship data from memory and determine that coil 112 corresponds 121 and in response, transfer the control signaling to sensor 121.

Sensor 121 operates in response to the control signals from controller 141. Coil 112 emits magnetic waves that form the coil magnetic field. The vapor cells of sensor 121 are positioned in the coil magnetic field. The vapor cells contain an alkali metal vapor like rubidium. The vapor cells may be heated by the heaters and be biased by the sensor coils. The pump laser emits a pump beam that is circularly polarized at a resonant frequency of the vapor to polarize the atoms. The probe laser emits a probe beam that is linearly polarized at a non-resonant frequency of the vapor to probe the atoms. The probe beam enters the vapor cells where quantum interactions with the atoms in the presence of the coil magnetic field alter the energy/frequency of probe beam by amounts that correlate to the field strength of the coil magnetic field. The photodetectors detect the probe beam after these alterations by the vapor atoms responsive to the coil magnetic field. The photodetectors generate and transfer corresponding analog electronic signals that characterize the field strength of the coil magnetic field. In some examples, a signal processor (not shown) may filter, amplify, digitize, or perform other tasks on the analog electronic signals. The photodetectors transfer an electronic signal that carries the data over cabling 131 to controller 141.

Controller 141 processes the electronic signal received from sensor 121 to generate data that characterizes the measured field strength of the coil magnetic field. The processor of controller 141 retrieves an executes the localization application from memory. The localization application correlates the field strength reported by sensor 121 to a distance between sensor 121 and coil 112. For example, the localization application may determine distance between sensor 121 and coil 112 is 24 millimeters based on the measured field strength. Although the example distance is given in millimeters, the localization application may operate on a more precise measurement scale like micrometers or nanometers. The localization application calculates the spatial location of sensor 121 based on the correlated distance, the known location of coil 112 on sensor mount 111, and the orientational and positional constrains of slot 114 on sensor 121. The localization application uses the spatial location of coil 112 and the orientation and location of slot 114 as reference points. For example, the localization application may execute a linearization function the receives the correlated distance, a direction vector of slot 114, and a known spatial location of coil 112 as inputs and outputs the spatial location of sensor 121. Controller 141 stores the spatial location of sensor 121 in the memory. Once sensor 121 is located, controller 141 may repeat the sensor localization process described above for other sensors on mount 121 until each sensor has been located.

Once all of sensors 121 are located and their spatial locations are stored in the memory of controller 141, controller 141 directs sensors 121 to measure the magnetic field generated by the neuronal activity of target 101. Sensors 121 measure the target magnetic field and report the measured field strengths to controller 141. Controller 141 initiates a source localization process to generate a MEG image based on the detected field strengths of the target magnetic field and the spatial locations of sensors 121. The transceiver circuitry of controller 141 may transfer the resulting MEG image to downstream systems. In some examples, controller 141 may display the MEG image on a user interface system of controller 141.

In some examples, the time taken for controller 141 to locate one of sensors 121 once sensors 121 have been conformed to the head of target 101 is on the order of one second. It should be appreciated that the total amount of time for controller 141 to localize each of sensors 121 depends in part on the total number on sensors. For example, if sensors 121 comprise ten individual sensors and sensors 121 are conformed to target 101, the localization process may take controller 141 around ten seconds to perform.

MEG system 100 may combine the electromagnetic coil-based sensor localization methods described above with other sensor localization methods. For example, MEG system 100 may utilize mechanical localization, optical localization, and/or other localization methods to augment the electromagnetic coil-based sensor localization.

In some examples, ratchet mechanisms 113 may comprise set screws with known locations on sensor mount 111 that move sensors 121 to conform to the shape of target 101 and fix the orientation and location of sensors 121. The set screws may comprise distance gauges that indicate how for the set screws have moved their corresponding ones of sensors 121. Controller 141 may receive the set screw data and determine the spatial locations of sensors 121 based on the known locations of the set screws and the distance indicated by the gauges. The gauges may be electronic and automatically report the distance to controller 141. Alternatively, the gauges may be entirely mechanical, and the distance may be manually read out and fed to controller 141 by a human operator. Controller 141 combines the set screw spatial localization with the coil-based sensor localization to improve the overall accuracy of the localizations.

In some examples, sensor mount 111 may comprise scannable fiduciary marks at multiple surface locations that define its location and orientation. A human operator may scan the fiduciary marks and input the scanned data into controller 141. Controller 141 may receive the scanned data and responsively determine the spatial locations of sensors 121. Controller 141 combines the optically scanned localization with the coil-based sensor localization to improve the overall accuracy of the localizations.

In some examples, cameras (not illustrated), may image sensors 121 from multiple orientations and transfer the image data to controller 141. Controller 141 ingests the images and generates a 3D model of sensor mount 111 based on the image data that depicts the location and orientation for each of sensors 121. Controller 141 determine the spatial locations of sensors 121 based on the image data and the 3D model. Controller 141 combines the image-based localization with the coil-based sensor localization to improve the overall accuracy of the localizations.

In some examples, a scanner may scan Radio Frequency (RF) IDs of sensors 121 and transfer the scanned data to controller 141. Controller 141 may process the RF data to determine the spatial locations of sensors 121. Controller 141 combines the RF-based localization with the coil-based sensor localization to improve the overall accuracy of the localizations.

In some examples, multiple ones of the aforementioned sensor localization techniques may be combined with the electromagnetic coil-based sensor localizations to determine the spatial locations of the sensors. For example, MEG system 100 may utilize a combination of coil-based localization, mechanical localization, and image-based localization to determine the spatial locations of sensors 121.

In some examples, controller 141 may determine the presence of sensors 121 on sensor mount 111. For example, sensor mount 111 may comprise additional ones of slots 114 and/or ones of sensors 121 may be improperly connected to sensor mount 111 and controller 141 may determine the presence of sensors 121 to determine which ones of slots 114 are occupied and/or which ones of sensors 121 are properly reading out magnetic field strengths. In this example, controller 141 selects one or more of coils 112 and supplies electrical current to the selected ones of coils 112 over cabling 131. For example, the processing circuitry of controller 141 may access a data structure stored by the memory that correlates sets of coils 112 to ones of slots 114 and select one of the sets to determine if one of sensors 121 is present in the slot and is functioning correctly. The sets of coils 112 may comprise one or more coils and the one or more coils may comprise one or more spatial orientations. The selected ones of coils 112 generate magnetic waves that form the coil magnetic field. Controller 141 transfers control signaling to sensors 121 to measure the strength of the coil magnetic field generated by the selected one of coils 112.

Each of sensors 121 operate in response to the control signals from controller 141 and measure the strength of the coil magnetic field as described above. Sensors 121 transfer data over cabling 131 that characterizes the strength of the measured coil magnetic field. Controller 141 processes the electronic signal received from sensors 121 to generate data that characterizes the measured field strength of the coil magnetic field. The processor of controller 141 retrieves and executes a sensor detection application (not illustrated) from memory. The sensor detection application correlates the measured field strengths to a presence of one of sensors 121 in the one of slots 114 that correlates to the selected ones of coils 112. For example, the sensor detection application may apply a strength threshold to the received field strength data from each of sensors 121. If the measured field strength from a particular sensor is below the strength threshold, the sensor detection application determines that the particular sensor does not reside in the one of slots 114 or if it does reside in the one of slots 114, is not reading out magnetic field strength. Likewise, if the measured field strength from a particular sensor is above the strength threshold, the sensor detection application determines that the particular sensor resides in the one of slots 114 that corresponds to the selected set of coils 112. The sensor detection application determines if the slot of slots 114 that corresponds to the selected ones of coils 112 is occupied by one of sensors 121 based on the reported magnetic field strengths received from sensors 121. Once the presence (or lack thereof) of the one of sensors 121 is confirmed, controller 141 repeats the sensor detection process described above for other ones of coils 112 and slots 114 on mount 111 until each sensor has been detected. The sensor detection application may correlate the sensor IDs of sensors 121 to the slots of slots 114 to map out the positions of sensors 121 on mount 111 and to correlate ones of sensors 121 to coil sets of coils 112 that correspond to the slots. In some examples, the sensor detection application and the localization application may comprise a single software application with detection and localization functionality.

FIG. 6 illustrates process 600. Process 600 is representative of localization process to determine the spatial locations of sensors in a conformal MEG apparatus. Portions of process 600 may be implemented in program instructions in the context of any of the hardware components, software applications, module components, or other such elements of one or more computing devices.

The operations of process 600 comprise supplying electric current to a coil set comprising one or more coils (step 601). The operations further comprise generating magnetic field waves that form at least one coil magnetic field that comprises magnetic field characteristics configured for a magnetic field sensor (step 602). The operations further comprise measuring the strength and the direction of the at least one coil magnetic field (step 603). The operations further comprise locating the magnetic field sensor based on the measured strength and the measured direction of the at least one coil magnetic field (step 604). In some examples, process 600 may repeats cyclically and returns to process step 601.

Referring back to FIGS. 1 and 5, MEG system 100 includes a brief example of process 600 as implemented by the various hardware and software components that comprise MEG system 100. The structure and operation of MEG system 100 may differ in other examples.

In operation, sensor mount 111 is placed on head of target 101. A human operator adjusts ratchet mechanisms 113 to drive sensors 121 through their respective ones of slots 114 until in contact with the scalp of target 101. The human operator locks ratchet mechanism 113 to constrain the positions of sensors 121 and conform sensors 121 to the shape of target 101. The human operator interacts with a user interface system of controller 141 to initiate sensor localization.

Controller 141 initiates a sensor localization process for sensor mount 111 in response to the user input. The processor of controller 141 retrieves sensor/coil data that correlates ones of sensors 121 with coil sets of coils 121 from memory. The sensor/coil data comprises an ordered list that correlates sensor IDs for ones of sensors 121 with coil IDs of coils 112. The processor selects one of the sensor/coil set pairs to localize that sensor. The processor transfers electric current to the coil set that corresponds to the selected sensor via cabling 131 (step 601).

The coil set receives the electric current and responsively generates magnetic field waves that form a set of magnetic fields configured for the selected sensor. For example, each of the magnetic fields may comprise a direction, a magnitude, and a gradient configured for the selected sensor. A portion of the coils of the coil set are configured to generate a homogenous magnetic field and another portion of the coils of the coil set are configured to generate a gradient magnetic field (step 602). The gradient magnetic field is directionally aligned with the sensor. The magnitude of the gradient magnetic field decreases as the distance from the coil generating the gradient magnetic field increases. The homogenous magnetic field is constant in both direction and magnitude. The gradient magnetic fields and the homogenous magnetic fields may differ in phase and/or amplitude or may comprise the same phase and amplitude.

Subsequently, the processor of controller 141 generates instructions that direct the selected sensor of sensors 121 to measure the gradient coil magnetic field and the homogenous coil magnetic field. The selected sensor receives the instruction and responsively measures the coil magnetic fields generated by the coil set (step 603). The vapor cells of the selected sensor are positioned in the gradient coil magnetic field and the homogenous coil magnetic field. The pump laser emits a pump beam that is circularly polarized at a resonant frequency of the vapor to polarize the atoms. The probe laser emits a probe beam that is linearly polarized at a non-resonant frequency of the vapor to probe the atoms.

The probe beam enters the vapor cells where quantum interactions with the atoms in the presence of the coil magnetic field alter the energy/frequency of probe beam by amounts that correlate to the field strength of the gradient coil magnetic field(s) and to the direction of the homogenous coil magnetic field(s). The photodetectors detect the probe beam after these alterations by the vapor atoms responsive to the coil magnetic field. The photodetectors generate corresponding electronic signals that characterize the field strength of the gradient coil magnetic field and the field direction of the homogenous coil magnetic field. The photodetectors transfer an electronic signal that carries the field characterization data over cabling 131 to controller 141.

The transceiver circuitry in controller 141 receives the signaling and stores the field characterization data in memory. The processor in in controller 141 retrieves and executes the localization application from memory. The localization application correlates the measured field strength of the gradient magnetic field to a distance between the coil set and the selected sensor. The localization application correlates the measured direction of the homogenous magnetic field to an orientation of the selected sensor. The localization application implements a function that receives the correlated distance, correlated orientation, and the known location of the coil set and outputs the spatial location of the selected sensor (step 604). The processor in controller 141 stores the determined spatial location of the selected sensor in memory in association with the sensor ID of the selected sensor. The processor retrieves the sensor/coil data from memory selects a second one of sensor/coil set pairs from the ordered list of coil set/sensor ID pairs to localize the next sensor. The processor transfers electric current to the coil set that corresponds to the next sensor via cabling 131 and repeats the above localization process to determine the spatial locations for each of sensors 121.

FIG. 7 illustrates process 700. Process 700 is representative of localization process to determine the spatial locations of sensors in a conformal MEG apparatus. Portions of process 700 may be implemented in program instructions in the context of any of the hardware components, software applications, module components, or other such elements of one or more computing devices.

The operations of process 700 comprise mounting a magnetic field sensor and mechanically constraining the magnetic field sensor in one or more degrees of freedom (step 701). The operations further comprise supplying electric current to a coil set comprising one or more coils (step 702). The operations further comprise generating magnetic field waves that form at least one coil magnetic in response to the electric current (step 703). The operations further comprise measuring a strength of the at least one coil magnetic field (step 704). The operations further comprise locating the magnetic field sensor based on the constraint and the measured strength of the at least one coil magnetic field (step 705). In some examples, process 700 may repeats cyclically and returns to process step 701.

Referring back to FIGS. 1 and 5, MEG system 100 includes a brief example of process 700 as implemented by the various hardware and software components that comprise MEG system 100. The structure and operation of MEG system 100 may differ in other examples.

In operation, sensor mount 111 is placed on head of target 101. A human operator adjusts ratchet mechanisms 113 to drive sensors 121 through their respective ones of slots 114 until in contact with the scalp of target 101. For example, the human operator may turn set screws to drive sensors 121 through slots 114. The shape, longitudinal direction, and location of slots 114 constrain the orientational degrees of freedom and two of the three positional degrees of freedom of sensors 121 (step 701). The human operator locks ratchet mechanism 113 to constrain the third positional degree of freedom of sensors 121. Ratchet mechanisms 113 and slots 114 conform sensors 121 to the shape of target 101. The human operator interacts with a user interface system of controller 141 to initiate sensor localization.

Controller 141 initiates a sensor localization process for sensor mount 111 in response to the user input. The processor of controller 141 retrieves sensor/coil data that correlates ones of sensors 121 with coil sets of coils 121 from memory. The sensor/coil data comprises an ordered list that correlates sensor IDs for ones of sensors 121 with coil IDs of coils 112. The processor selects one of the sensor/coil set pairs to localize that sensor. The processor transfers electric current to the coil set that corresponds to the selected sensor via cabling 131 (step 702). The coil set receives the electric current and responsively generates magnetic field waves that form a coil magnetic field. The coil set generates a gradient magnetic field that is directionally aligned with the selected sensor (step 703). The magnitude of the gradient magnetic field decreases as the distance from the coil generating the gradient magnetic field increases.

Subsequently, the processor of controller 141 generates instructions that direct the selected sensor of sensors 121 to measure the strength of the gradient coil magnetic field. The selected sensor receives the instruction and responsively measures the gradient magnetic field generated by the coil set (step 704). The vapor cells of the selected sensor are positioned in the gradient coil magnetic field. The pump laser emits a pump beam that is circularly polarized at a resonant frequency of the vapor to polarize the atoms. The probe laser emits a probe beam that is linearly polarized at a non-resonant frequency of the vapor to probe the atoms. The probe beam enters the vapor cells where quantum interactions with the atoms in the presence of the gradient magnetic field alter the energy/frequency of probe beam by amounts that correlate to the field strength of the gradient coil magnetic field. The photodetectors detect the probe beam after these alterations by the vapor atoms responsive to the coil magnetic field. The photodetectors generate corresponding electronic signals that characterize the field strength of the gradient coil magnetic field. The photodetectors transfer an electronic signal that carries the field characterization data over cabling 131 to controller 141.

The transceiver circuitry in controller 141 receives the signaling and stores the field characterization data in memory in association with the sensor ID of the selected sensor. The processor in in controller 141 retrieves and executes the localization application from memory. The localization application correlates the measured field strength of the gradient magnetic field to a distance between the coil set and the selected sensor. The localization application retrieves coil location data from memory that indicates the spatial location on sensor mount 111 of the coil set associated with the selected sensor. The localization application retrieves sensor orientation data that characterizes the orientation of the selected sensor based on the longitudinal direction of a corresponding one of slots 114. The localization application implements a function that receives the correlated distance, the spatial location of the coil set, and the orientation of the selected sensor as inputs and outputs the spatial location of the selected sensor (step 705). The processor in controller 141 stores the determined spatial location of the selected sensor in memory in association with its sensor ID. The processor retrieves the sensor/coil data from memory and selects a next one of sensor/coil set pairs from the ordered list to localize the next sensor. The processor transfers electric current to the coil set that corresponds to the next sensor via cabling 131 and repeats the above localization process to determine the spatial locations for each of sensors 121.

Figure 8:
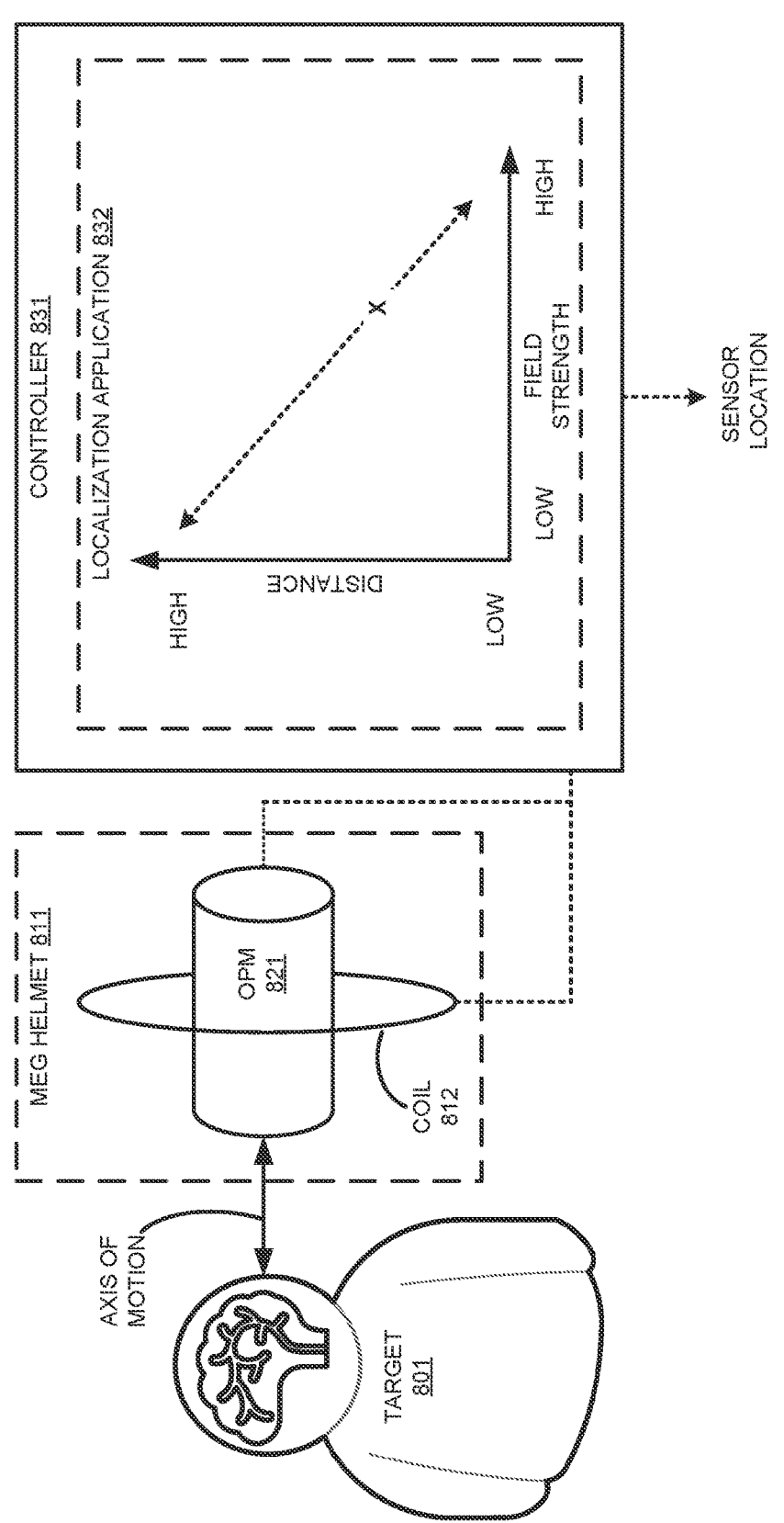
FIG. 8 illustrates an exemplary MEG system.

FIG. 8 illustrates MEG system 800. MEG system 800 is an example MEG system 100 illustrated in FIG. 1, although the MEG system 100 may differ. MEG system 800 comprises target 801, MEG helmet 811, coil 812, OPM 821, and controller 831. Controller 831 is representative of one or more computing devices configured to host localization application 832.

MEG helmet 811 comprises OPM 821 and coil 812. OPM 821 and coil 812 are communicatively coupled to controller 831. The communication links may comprise wired links, wireless links, or a combination thereof. Controller 831 hosts localization application 832 that implements the graph illustrated in FIG. 8. The horizontal axis of the graph indicates a field strength in an exemplary range: Low to High. The vertical axis of the graph indicates a distance in an exemplary range: Low to High. These terms are illustrative and numerical values could be used. As indicated by the X mark on the graph, measured field strength of the coil magnetic field generated by the coil 812 correlates to a distance between OPM 821 and coil 812. In this example, the reported field strength inversely correlates to the distance. As shown on the graph, a high measured field strength indicates a low distance, and a low measured field strength indicates a high distance. Typically, the closer OPM 821 is to the helmet coil loop, the higher the reported magnetic field strength will be. Localization application 832 may correlate the field strength to the distance by theoretical magnetic field modelling or experimentally through a calibration process. For example, controller 831 may direct OPM sensor 821 to measure the coil magnetic field strength at multiple locations along its axis of motion and responsively determine a magnetic field gradient with respect to distance.

In operation, controller 831 powers coil 812 and coil 812 responsively generates a gradient magnetic field directionally aligned with the axis of motion of OPM 821. OPM 821 moves from its origin along its axis of motion to a location proximate to target 801 and measures the strength of the coil magnetic field. MEG helmet 811 constrains the orientation and location of OPM 821 to restrict the movement of OPM 821 of along its axis of motion. OPM 821 transfers signaling that indicates the measured field strength to the controller 831. Controller 831 implements localization application 832. Localization application 832 applies the data structure illustrated in FIG. 8 to correlate the reported field strength to the distance between coil 812 and OPM 821. Localization application 832 determines the location of OPM 821 based on the distance indicated by the data structure and the location of the coil 811. The location of coil 811 indicates a known reference point and comprises a spatial location on and/or in the helmet. Controller 831 processes the distance, the axis of motion of OPM 821, and the spatial location of coil 812 to identify the spatial location of OPM 821. Localization application 832 may utilize an algorithmic process that takes correlated distance, direction of motion, and coil reference location as inputs and outputs the spatial location of OPM 821. Controller 821 typically repeats the sensor location process for other OPMs on helmet 811 until each OPM is located. OPM controller 821 may locate one OPM at a time to inhibit magnetic fields generated by different coils loops interfering with field strength measurements of different OPMs. Once OPM 821 is located, the controller 831 stops supplying current to the coil and localizes a next OPM. Alternatively, controller may locate multiple OPMs simultaneously. For example, controller 831 may supply current to multiple coils in helmet 811 that correspond to different OPMs in helmet 811. The multiple coils may generate magnetic fields at different frequencies and/or different phases to inhibit measurement interference between the OPMs. By localizing multiple OMPs simultaneously, the time to localize each OPM in the sensor array of MEG helmet 811 is further reduced.

Figure 9:
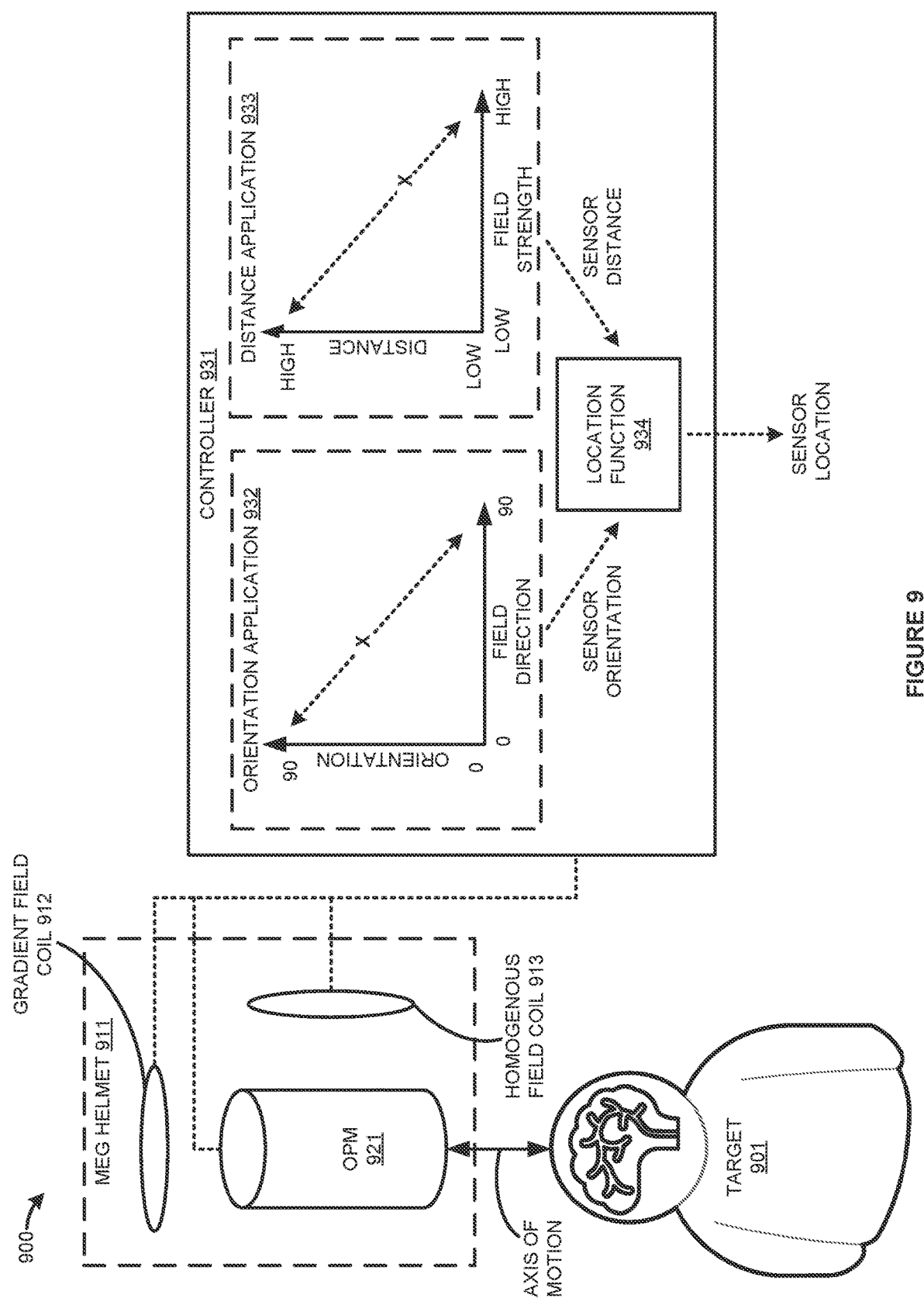
FIG. 9 illustrates an exemplary MEG system.

FIG. 9 illustrates MEG system 900. MEG system 900 is an example MEG system 100 illustrated in FIG. 1, although the MEG system 100 may differ. MEG system 900 comprises target 901, MEG helmet 911, gradient field coil 912, homogenous field coil 913, OPM 921, and controller 931. Gradient field coil 912 and homogenous field coil 913 form a coil set and comprise differing positions and orientations. Controller 931 is representative of one or more computing devices configured to host orientation application 932, distance application 933, and location function 934.

MEG helmet 911 comprises OPM 921, gradient field coil 912, and homogenous field coil 913. OPM 921 and coils 912-913 are communicatively coupled to controller 931. The communication links may comprise wired links, wireless links, or a combination thereof. Controller 931 hosts orientation application 932 that implements the graph illustrated in FIG. 9. The horizontal axis of the graph indicates a field direction in an exemplary range: 0° to 90°. The vertical axis of the graph indicates a sensor orientation in an exemplary range: 0° to 90°. These terms are illustrative and other values could be used. As indicated by the X mark on the graph, measured field direction of the homogenous coil magnetic field generated by the coil 913 correlates to a sensor orientation of OPM 921. In this example, the reported angular direction of the field correlates to an OPM angular direction. As shown on the graph, a high measured field angle indicates an OPM orientation perpendicular to the direction of the field, and a low measured field angle indicates an OPM orientation parallel with the field direction. Orientation application 932 outputs a sensor orientation to location function 934.

Controller 931 hosts distance application 933 that implements the graph illustrated in FIG. 9. The horizontal axis of the graph indicates a field strength in an exemplary range: Low to High. The vertical axis of the graph indicates a distance in an exemplary range: Low to High. These terms are illustrative and numerical values could be used. As indicated by the X mark on the graph, measured field strength of the gradient coil magnetic field generated by the coil 912 correlates to a distance between OPM 921 and coil 912. In this example, the reported field strength inversely correlates to the distance. As shown on the graph, a high measured field strength indicates a low distance, and a low measured field strength indicates a high distance. The closer OPM 921 is to the helmet coil loop, the higher the reported magnetic field strength will be. Location application 932 may correlate the field strength to the distance by theoretical magnetic field modelling or experimentally through a calibration process. Distance application 933 outputs a sensor distance to location function 934.

Controller 931 hosts location function 934. Location function 934 receives sensor orientation output by orientation application 932 and sensor distance output by distance application 933 as inputs. Location function 934 calculates the spatial location of OPM 921 based on the orientation of sensor 921, the distance between gradient field coil 912 and OPM 921, and the spatial location of coil 912. Location function 934 may comprise a linearization function that the receives the correlated distance, a direction vector of OPM 921 based on the correlated orientation, and a known spatial location of coil 912 as inputs and outputs the spatial location of sensor 921.

In operation, controller 931 sequentially powers coils 912 and coil 913. Coil 912 generates a gradient magnetic field aligned with the axis of motion of OPM 921. Coil 913 generates a homogenous magnetic field that is uniform in both direction and magnitude. OPM 921 moves from its origin along its axis of motion to a location proximate to target 901. OPM 921 measures the direction of the homogenous coil magnetic field. OPM 921 transfers signaling that indicates the measured field direction to the controller 931. OPM 921 measures the strength of the gradient coil magnetic field. OPM 921 transfers signaling that indicates the measured field strength to the controller 931. Controller 931 implements orientation application 932, distance application 933, and location function 934. Orientation application 932 applies the data structure illustrated in FIG. 9 to correlate the reported field direction to a spatial orientation of OPM 921. Distance application 933 applies the data structure illustrated in FIG. 9 to correlate the reported field strength to the distance between coil 912 and OPM 921. Location function 934 processes the correlated distance, correlated OPM orientation, and the known location of gradient field coil 912 to determine the spatial location of OPM 921. In some examples, gradient coil 912 and homogenous coil 913 may comprise a single coil with a homogenous operating mode and a gradient operating mode. For example, controller 931 may vary the current level supplied to the dual mode coil to change between a homogenous field generation mode and a gradient field generation mode. In some examples, MEG system 900 may comprise additional homogenous magnetic field coils at additional spatial locations and orientations to generate multiple homogenous magnetic fields with varying directions in the vicinity of OPM 921 to increase the accuracy of the orientation correlation performed by orientation application 932.

FIG. 10 illustrates environment 1000. Environment 1000 illustrates an exemplary operation of magnetometers in a gradient magnetic field and homogenous magnetic field. Environment 1000 comprises gradient magnetic field 1001, homogenous magnetic field 1002, gradient field coil 1011, homogenous field coil 1012, and OPMs 1021-1022. Gradient field coil 1011 generates gradient magnetic field 1001 and homogenous field coil 1012 generates homogeneous magnetic field 1002. OPM 1021 is positioned within gradient magnetic field 1001 and OPM 1022 is positioned in homogenous magnetic field 1002. Magnetic fields 1001-1002 are represented by arrows. The arrows may represent the field vectors that comprise magnetic fields 1001-1002. The direction of the arrows indicates the direction of the fields. The length of the arrows indicates the magnitude of the magnetic fields. Gradient magnetic fields vary in magnitude and/or direction over a region of interest while homogenous magnetic fields are constant in magnitude and direction over a region of interest. In particular, the region of interest may comprise the spatial location of a magnetic field sensor like OPMs 1021-1022. As illustrated in FIG. 10, the magnitude of gradient magnetic field 1001 decreases as the distance from gradient field coil 1011 increases. In contrast, the magnitude of homogeneous magnetic field 1002 remains constant as the distance from homogenous field coil 1011 increases.

OPM 1021 may measure the strength of gradient magnetic field 1021. Since the magnitude of gradient magnetic field 1001 varies with distance, the measured field strength may be used to determine the distance between OPM 1021 and gradient field coil 1011. OPM 1022 may measure the direction of homogenous magnetic field 1022. Since both the magnitude and direction of homogenous magnetic field 1002 are constant, the measured field direction can be used to determine the orientation of OPM 1022 with respect to homogenous magnetic field 1002. It should be appreciated that because the field direction of gradient magnetic field 1001 is not constant at the location of OPM 1021, the orientation of OPM 1021 cannot be effectively determined by measuring the direction of gradient magnetic field 1001. Likewise, because the field magnitude of homogeneous magnetic field 1002 is constant at the location of OPM 1022, the distance between OPM 1022 and homogeneous field coil 1012 cannot be effectively determined by measuring the strength of homogenous magnetic field 1002.

In some examples, gradient field coil 1011 and homogenous field coil 1012 may comprise a single magnetic field source with dual operating modes and OPMs 1021-1022 may comprise a single OPM magnetic field sensor. In this example, the dual mode field source comprises a known spatial location and first generates homogenous magnetic field 1002 at the location of the OPM. The OPM measures the direction of homogenous magnetic field 1002 and reports the measured field direction to a device controller (not illustrated). The dual mode magnetic field source stops generating homogenous magnetic field 1002, switches operating modes (e.g., by varying power), and generates gradient magnetic field 1001. The OPM measures the strength of gradient magnetic field 1001 and reports the measured field strength to the device controller. The device controller determines the spatial location and orientation of the OPM based the known spatial location of the dual mode field source, the measured field strength, and the measured field direction.

In some examples, environment 1000 may comprise multiple homogenous field coils. The multiple homogenous field coils may be positioned at different orientations to generate homogenous magnetic fields with varying directions. OPM 1022 may detect the direction of each of the multiple homogenous magnetic fields. By increasing the number of homogenous fields at different directions, the orientation of OPM 1022 can be more precisely determined. For example, a device controller may process the measured field directions of the multiple homogenous magnetic fields and correlate the detected field directions to the roll, pitch, and yaw of OPM 1022 to determine the orientation of sensor 1022.

Figure 11:
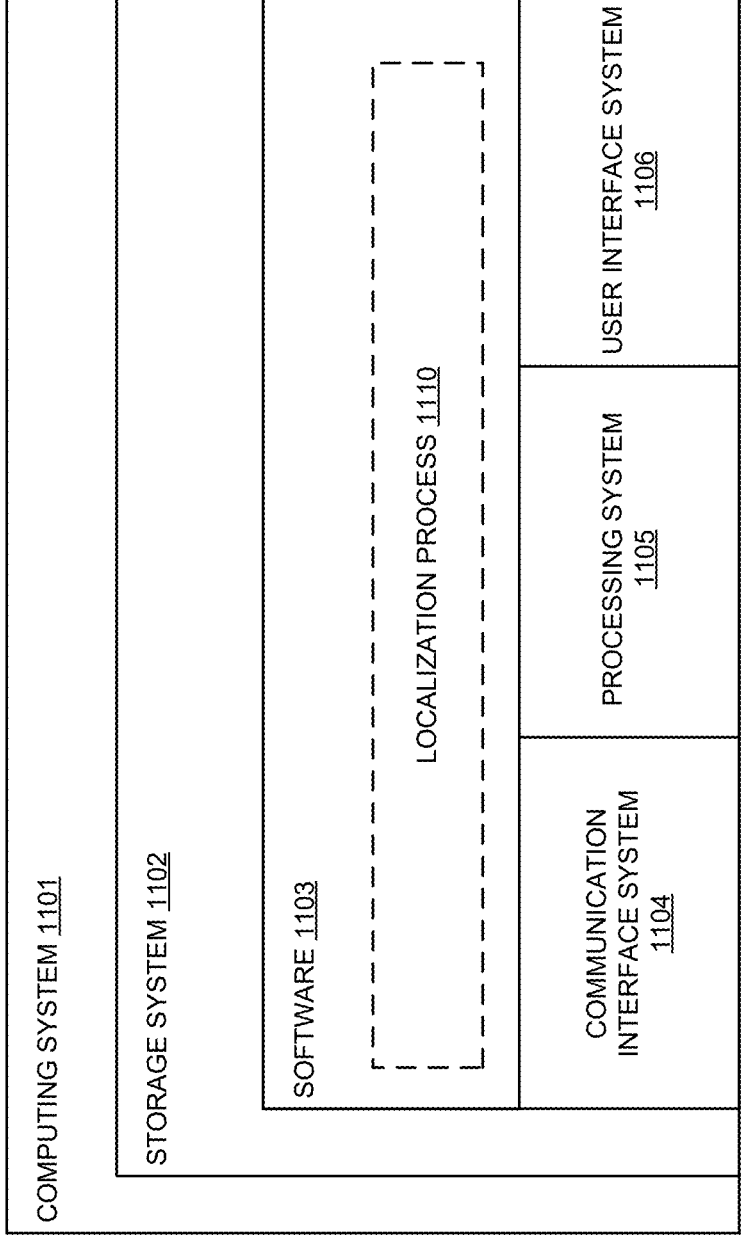
FIG. 11 illustrates an exemplary computing apparatus according to some embodiments.

FIG. 11 illustrates computing system 1101 according to an implementation of the present technology. Computing system 1101 is representative of any system or collection of systems in which the various processes, programs, services, and scenarios disclosed herein for localizing sensors in conformal MEG may be implemented. For example, computing system 1101 may be representative of controller 141, controller 831, controller 931, and/or any other computing device contemplated herein. Examples of computing system 1101 include, but are not limited to, computers, servers, network controllers, web servers, and cloud computing platforms, as well as any other type of physical or virtual server machine, physical or virtual router, container, and any variation or combination thereof. Computing system 1101 may be implemented as a single apparatus, system, or device or may be implemented in a distributed manner as multiple apparatuses, systems, or devices. Computing system 1101 includes, but is not limited to storage system 1102, software 1103, communication interface system 1104, processing system 1105, and user interface system 1106. Processing system 1105 is operatively coupled with storage system 1102, communication interface system 1104, and user interface system 1106.

Processing system 1105 loads and executes software 1103 from storage system 1102. Software 1103 includes and implements localization process 1110, which is representative of the sensor localization processes discussed with respect to the preceding Figures including portions of process 600 illustrated in FIG. 6 and portions of process 700 illustrated in FIG. 7. When executed by processing system 1105, software 1103 directs processing system 1105 to operate as described herein for at least the various processes, operational scenarios, and sequences discussed in the foregoing implementations. Computing system 1101 may optionally include additional devices, features, or functionality not discussed here for purposes of brevity.

Processing system 1105 may comprise a micro-processor and other circuitry that retrieves and executes software 1103 from storage system 1102. Processing system 1105 may be implemented within a single processing device but may also be distributed across multiple processing devices or subsystems that cooperate in executing program instructions. Examples of processing system 1105 include general purpose CPUs, GPUs, DSPs, ASICs, FPGAs, and logic devices, as well as any other type of processing device, combinations, or variations thereof.

Storage system 1102 may comprise any computer readable storage media that is readable by processing system 1105 and capable of storing software 1103. Storage system 1102 may include volatile and nonvolatile, removable, and non-removable media implemented in any method or technology for storage of information, such as computer readable instructions, data structures, program modules, or other data. Examples of storage media include RAM, read only memory, magnetic disks, optical disks, optical media, flash memory, virtual memory and non-virtual memory, magnetic cassettes, magnetic tape, magnetic disk storage or other magnetic storage devices, or any other suitable storage media. In no case is the computer readable storage media a propagated signal.

In addition to computer readable storage media, in some implementations storage system 1102 may also include computer readable communication media over which at least some of software 1103 may be communicated internally or externally. Storage system 1102 may be implemented as a single storage device but may also be implemented across multiple storage devices or sub-systems co-located or distributed relative to each other. Storage system 1102 may comprise additional elements, such as a controller, capable of communicating with processing system 1105 or possibly other systems.

Software 1103 (localization process 1110) may be implemented in program instructions and among other functions may, when executed by processing system 1105, direct processing system 1105 to operate as described with respect to the various operational scenarios, sequences, and processes illustrated herein. For example, software 1103 may include program instructions for correlating a measured magnetic field strength to a distance and determining the spatial location of a magnetic field sensor based on the correlated distance, orientation constraints on the sensor, and the spatial location of the magnetic field source.

In particular, the program instructions may include various components or modules that cooperate or otherwise interact to carry out the various processes and operational scenarios described herein. The various components or modules may be embodied in compiled or interpreted instructions, or in some other variation or combination of instructions. The various components or modules may be executed in a synchronous or asynchronous manner, serially or in parallel, in a single threaded environment or multi-threaded, or in accordance with any other suitable execution paradigm, variation, or combination thereof. Software 1103 may include additional processes, programs, or components, such as operating system software, virtualization software, or other application software. Software 1103 may also comprise firmware or some other form of machine-readable processing instructions executable by processing system 1105.

In general, software 1103 may, when loaded into processing system 1105 and executed, transform a suitable apparatus, system, or device (of which computing system 1101 is representative) overall from a general-purpose computing system into a special-purpose computing system customized to localize magnetic field sensors like OPMs in a conformal MEG apparatus. Indeed, encoding software 1103 on storage system 1102 may transform the physical structure of storage system 1102. The specific transformation of the physical structure may depend on various factors in different implementations of this description. Examples of such factors may include, but are not limited to, the technology used to implement the storage media of storage system 1102 and whether the computer-storage media are characterized as primary or secondary storage, as well as other factors.

For example, if the computer readable storage media are implemented as semiconductor-based memory, software 1103 may transform the physical state of the semiconductor memory when the program instructions are encoded therein, such as by transforming the state of transistors, capacitors, or other discrete circuit elements constituting the semiconductor memory. A similar transformation may occur with respect to magnetic or optical media. Other transformations of physical media are possible without departing from the scope of the present description, with the foregoing examples provided only to facilitate the present discussion.

Communication interface system 1104 may include communication connections and devices that allow for communication with other computing systems (not shown) over communication networks (not shown). Examples of connections and devices that together allow for inter-system communication may include network interface cards, antennas, power amplifiers, RF circuitry, transceivers, and other communication circuitry. The connections and devices may communicate over communication media to exchange communications with other computing systems or networks of systems, such as metal, glass, air, or any other suitable communication media. The aforementioned media, connections, and devices are well known and need not be discussed at length here.

Communication between computing system 1101 and other computing systems (not shown), may occur over a communication network or networks and in accordance with various communication protocols, combinations of protocols, or variations thereof. Examples include intranets, internets, the Internet, local area networks, wide area networks, wireless networks, wired networks, virtual networks, software defined networks, data center buses and backplanes, or any other type of network, combination of network, or variation thereof. The aforementioned communication networks and protocols are well known and need not be discussed at length here.

While some examples provided herein are described in the context of computing devices for localizing magnetic field sensors based on measured field strength, measured field orientation, and magnetic field source locations, it should be understood that the systems and methods described herein are not limited to such embodiments and may apply to a variety of other magnetometry environments and their associated systems. As will be appreciated by one skilled in the art, aspects of the present invention may be embodied as a system, method, computer program product, and other configurable systems. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number, respectively. The word "or" in reference to a list of two or more items, covers all of the following interpretations of the word: any of the items in the list, all of the items in the list, and any combination of the items in the list.

The phrases "in some embodiments," "according to some embodiments," "in the embodiments shown," "in other embodiments," and the like generally mean the particular feature, structure, or characteristic following the phrase is included in at least one implementation of the present technology and may be included in more than one implementation. In addition, such phrases do not necessarily refer to the same embodiments or different embodiments.

The above Detailed Description of examples of the technology is not intended to be exhaustive or to limit the technology to the precise form disclosed above. While specific examples for the technology are described above for illustrative purposes, various equivalent modifications are possible within the scope of the technology, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented in parallel or may be performed at different times. Further any specific numbers noted herein are only examples: alternative implementations may employ differing values or ranges.

The teachings of the technology provided herein can be applied to other systems, not necessarily the system described above. The elements and acts of the various examples described above can be combined to provide further implementations of the technology. Some alternative implementations of the technology may include not only additional elements to those implementations noted above, but also may include fewer elements.

These and other changes can be made to the technology in light of the above Detailed Description. While the above description describes certain examples of the technology, and describes the best mode contemplated, no matter how detailed the above appears in text, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the above Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while only one aspect of the technology is recited as a method claim, other aspects may likewise be embodied as a computer-readable medium claim, or in other forms, such as being embodied in a means-plus-function claim. Any claims intended to be treated under 35 U.S.C. § 112(f) will begin with the words "means for" but use of the term "for" in any other context is not intended to invoke treatment under 35 U.S.C. § 112(f). Accordingly, the applicant reserves the right to pursue additional claims after filing this application to pursue such additional claim forms, in either this application or in a continuing application.

What is claimed is:

1. A method to determine a location of a magnetic field sensor, the method comprising:
   mounting, by a Magnetoencephalography (MEG) helmet, the magnetic field sensor in a sensor slot of the MEG helmet, wherein the sensor slot fixes an orientation of the magnetic field sensor and restricts the magnetic field sensor to a single axis of motion;
   moving, by the magnetic field sensor, through the sensor slot along the single axis of motion to be proximate to or in contact with a surface of a target;
   supplying, by a controller, current to a coil attached to the MEG helmet at a known location;
   generating, by the coil, a coil magnetic field, wherein a strength of the coil magnetic field varies along the single axis of motion of the magnetic field sensor;
   measuring, by the magnetic field sensor, the strength of the coil magnetic field; and
   determining, by the controller, the location of the magnetic field sensor based on inputs comprising the single axis of motion of the magnetic field sensor, the known location of the coil, and the strength of the coil magnetic field measured by the magnetic field sensor.

2. The method of claim 1 further comprising:

corelating, by the controller, the strength of the coil magnetic field measured by the magnetic field sensor to a distance between the magnetic field sensor and the known location of the coil; and wherein:

determining, by the controller, the location of the magnetic field sensor based on the inputs comprising the single axis of motion of the magnetic field sensor, the known location of the coil, and the strength of the coil magnetic field measured by the magnetic field sensor comprises determining, by the controller, the location of the magnetic field sensor based on the inputs comprising the single axis of motion of the magnetic field sensor, the known location of the coil, and the distance between the magnetic field sensor and the known location of the coil.

3. The method of claim 2 further comprising:

implementing, by the controller, an algorithmic process that takes the single axis of motion of the magnetic field sensor, the known location of the coil, and the distance between the magnetic field sensor and the known location of the coil as the inputs and outputs the location of the magnetic field sensor; and wherein:

determining, by the controller, the location of the magnetic field sensor based on the inputs comprising the single axis of motion of the magnetic field sensor, the known location of the coil, and the distance between the magnetic field sensor and the known location of the coil comprises providing, by the controller, the single axis of motion of the magnetic field sensor, the known location of the coil, and the distance between the magnetic field sensor and the known location of the coil to the algorithmic process as the inputs and receiving, by the controller, the location of the magnetic field sensor as an output from the algorithmic process.

4. The method of claim 2 further comprising:

prior to moving, by the magnetic field sensor, through the sensor slot to be proximate to the surface of the target:

positioning, by the magnetic field sensor, in the sensor slot at a start location;

measuring, by the magnetic field sensor, a first strength of the coil magnetic field at the start location;

moving, by the magnetic field sensor, through the sensor slot to a second location;

measuring, by the magnetic field sensor, a second strength of the coil magnetic field at the second location; and determining, by the controller, a gradient of the coil magnetic field based on a difference between the first strength of the coil magnetic field at the start location and the second strength of the coil magnetic field at the second location; and wherein:

correlating, by the controller, the strength of the coil magnetic field to the distance between the magnetic field sensor and the coil comprises correlating, by the controller, the strength of the coil magnetic field to the distance between the magnetic field sensor and the coil based on the gradient of the coil magnetic field.

5. The method of claim 1 further comprising:

measuring, by the magnetic field sensor, a target strength of a target magnetic field generated by the target; and determining, by the controller, a source location of the target magnetic field based on the target strength of the target magnetic field and the location of the magnetic field sensor.

6. The method of claim 1 wherein the magnetic field sensor comprises an Optically Pumped Magnetometer (OPM).

7. The method of claim 1 wherein the magnetic field sensor comprises a gradiometer.

8. A system to determine a location of a magnetic field sensor, the system comprising:

a Magnetoencephalography (MEG) helmet, the magnetic field sensor, a coil, and a controller;

the MEG helmet configured to mount the magnetic field sensor in a sensor slot of the MEG helmet, wherein the sensor slot fixes an orientation of the magnetic field sensor and restricts the magnetic field sensor to a single axis of motion;

the magnetic field sensor configured to move through the sensor slot along the single axis of motion to be proximate to or in contact with a surface of a target;

the controller configured to supply current to the coil, wherein the coil is attached to the MEG helmet at a known location;

the coil configured to generate a coil magnetic field, wherein a strength of the coil magnetic field varies along the single axis of motion of the magnetic field sensor;

the magnetic field sensor further configured to measure the strength of the coil magnetic field; and the controller further configured to determine the location of the magnetic field sensor based on inputs comprising the single axis of motion of the magnetic field sensor, the known location of the coil, and the strength of the coil magnetic field measured by the magnetic field sensor.

9. The system of claim 8 wherein the controller is further configured to:

correlate the strength of the coil magnetic field measured by the magnetic field sensor to a distance between the magnetic field sensor and the known location of the coil; and determine the location of the magnetic field sensor based on the inputs comprising the single axis of motion of the magnetic field sensor, the known location of the coil, and the distance between the magnetic field sensor and the known location of the coil.

10. The system of claim 9 wherein the controller is further configured to:

implement an algorithmic process that takes the single axis of motion of the magnetic field sensor, the known location of the coil, and the distance between the magnetic field sensor and the known location of the coil as the inputs and outputs the location of the magnetic field sensor;

provide the single axis of motion of the magnetic field sensor, the known location of the coil, and the distance between the magnetic field sensor and the known location of the coil to the algorithmic process as the inputs; and receive the location of the magnetic field sensor as an output from the algorithmic process.

11. The system of claim 9 wherein:

the magnetic field sensor is further configured to:

position itself in the sensor slot at a start location;

measure a first strength of the coil magnetic field at the start location;

move through the sensor slot to a second location; and measure a second strength of the coil magnetic field at the second location; and the controller is further configured to:

determine a gradient of the coil magnetic field based on a difference between the first strength of the coil magnetic field at the start location and the second strength of the coil magnetic field at the second location; and correlate the strength of the coil magnetic field to the distance between the magnetic field sensor and the coil based on the gradient of the coil magnetic field.

12. The system of claim 8 wherein:

the magnetic field sensor is further configured to measure a target strength of a target magnetic field generated by the target; and the controller is further configured to determine a source location of the target magnetic field based on the target strength of the target magnetic field and the location of the magnetic field sensor.

13. The system of claim 8 wherein the magnetic field sensor comprises an Optically Pumped Magnetometer (OPM).

14. The system of claim 8 wherein the magnetic field sensor comprises a gradiometer.

15. A system to determine locations of magnetic field sensors, the system comprising:

a Magnetoencephalography (MEG) helmet, the magnetic field sensors, coils, and a controller;

the MEG helmet configured to mount the magnetic field sensors in sensor slots of the MEG helmet, wherein the sensor slots fix orientations of the magnetic field sensors and restrict the magnetic field sensors to single axes of motion;

the magnetic field sensors configured to move through their respective sensor slots along their respective single axes of motion to be proximate to or in contact with a surface of a target;

the controller configured to supply current to the coils, wherein the coils are attached to the MEG helmet at known locations;

the coils configured to generate coil magnetic fields, wherein strengths of the coil magnetic fields vary along the single axes of motion of the magnetic field sensors;

the magnetic field sensors further configured to measure the strengths of the coil magnetic fields; and the controller further configured to determine the locations of the magnetic field sensors based on inputs comprising the single axes of motion of the magnetic field sensors, the known locations of the coils, and the strengths of the coil magnetic fields measured by the magnetic field sensors.

16. The system of claim 15 wherein:

the controller is further configured to supply the current to the coils simultaneously;

the coils are further configured to simultaneously generate the coil magnetic fields at different frequencies in response to receiving the current;

the magnetic field sensors are further configured to measure the strengths of the coil magnetic fields generated at the different frequencies; and the controller is further configured to determine the locations of the magnetic field sensors based on the inputs comprising the single axes of motion of the magnetic field sensors, the known locations of the coils, and the strengths of the coil magnetic fields generated at the different frequencies measured by the magnetic field sensors.

17. The system of claim 15 wherein:

the controller is further configured to supply the current to the coils simultaneously;

the coils are further configured to simultaneously generate the coil magnetic fields at different phases in response to receiving the current;

the magnetic field sensors are further configured to measure the strengths of the coil magnetic fields generated at the different phases; and the controller is further configured to determine the locations of the magnetic field sensors based on the inputs comprising the single axes of motion of the magnetic field sensors, the known locations of the coils, and the strengths of the coil magnetic fields generated at the different phases measured by the magnetic field sensors.

18. The system of claim 15 wherein:

the controller is further configured to supply the current to the coils simultaneously;

the coils are further configured to simultaneously generate the coil magnetic fields at a same frequency and a same phase in response to receiving the current;

the magnetic field sensors are further configured to measure the strengths of the coil magnetic fields generated at the same frequency the same phase; and the controller is further configured to determine the locations of the magnetic field sensors based on the inputs comprising the single axes of motion of the magnetic field sensors, the known locations of the coils, and the strengths of the coil magnetic fields generated at the same frequency the same phase measured by the magnetic field sensors.

19. The system of claim 15 wherein individual ones of the magnetic field sensors correspond to individual ones of the coils on a one-to-one basis.

20. The system of claim 15 wherein:

the magnetic field sensors are further configured to measure a target strength of a target magnetic field generated by the target; and the controller is further configured to determine a source location of the target magnetic field based on the target strength of the target magnetic field and the locations of the magnetic field sensors.

* * * * *